(12) United States Patent
Wang et al.

(10) Patent No.: US 10,947,264 B2
(45) Date of Patent: Mar. 16, 2021

(54) PROCESS FOR PREPARATION OF SULFONYLUREA BILE ACID DERIVATIVES

(71) Applicant: Enanta Pharmaceuticals, Inc., Watertown, MA (US)

(72) Inventors: Guoqiang Wang, Belmont, MA (US); Yong He, Lexington, MA (US); Peng Dai, Auburndale, MA (US); Guoyou Xu, Framingham, MA (US); Bin Wang, Newton, MA (US); Jiang Long, Wayland, MA (US); Yat Sun Or, Waltham, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 16/784,296

(22) Filed: Feb. 7, 2020

(65) Prior Publication Data
US 2020/0247839 A1   Aug. 6, 2020

Related U.S. Application Data

(62) Division of application No. 15/826,233, filed on Nov. 29, 2017, now Pat. No. 10,584,145.
(Continued)

(51) Int. Cl.
*C07J 41/00* (2006.01)
*C07J 51/00* (2006.01)
*C07J 9/00* (2006.01)

(52) U.S. Cl.
CPC ........... *C07J 41/0055* (2013.01); *C07J 9/005* (2013.01); *C07J 41/0088* (2013.01); *C07J 51/00* (2013.01)

(58) Field of Classification Search
CPC .... C07J 41/0055; C07J 9/005; C07J 41/0088; C07J 51/00
See application file for complete search history.

(56) References Cited

U.S. PATENT DOCUMENTS

| 4,202,876 A | 5/1980 | Monks et al. |
| 5,466,815 A | 11/1995 | Enhsen et al. |

(Continued)

FOREIGN PATENT DOCUMENTS

| CN | 106478759 A | 3/2017 |
| CN | 106518946 A | 3/2017 |

(Continued)

OTHER PUBLICATIONS

"Mosesin-4' at www.chemspider.com/Chemical-Structure.10375019.html (retrieved from the internet Oct. 11, 2016)."
(Continued)

Primary Examiner — Paul A Zucker
(74) Attorney, Agent, or Firm — Edgar W. Harlan; Carolyn S. Elmore; Elmore Patent Law Group, P.C.

(57) ABSTRACT

The present invention relates to compounds of Formulas 3-6,

3

4

5

6

(Continued)

where $R_4$ $PG_1$ and $PG_2$ are defined as disclosed herein. These compounds are useful as intermediates in processes for preparing a compound of Formula I:

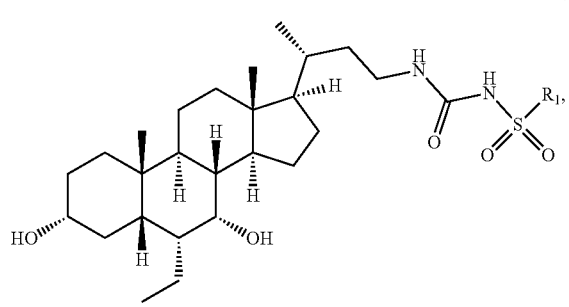

(I)

where $R_1$ is defined as disclosed herein.

5 Claims, 10 Drawing Sheets

Related U.S. Application Data

(60) Provisional application No. 62/427,354, filed on Nov. 29, 2016.

(56) References Cited

U.S. PATENT DOCUMENTS

| | | | |
|---|---|---|---|
| 5,512,558 | A | 4/1996 | Enhsen et al. |
| 5,541,348 | A | 7/1996 | Ayra et al. |
| 5,646,316 | A | 7/1997 | Jacobson et al. |
| 5,656,277 | A | 8/1997 | Berlati et al. |
| 7,858,608 | B2 | 12/2010 | Pellicciari et al. |
| 10,208,081 | B2 | 2/2019 | Wang et al. |
| 10,457,703 | B2 | 10/2019 | Wang et al. |
| 10,472,386 | B2 | 11/2019 | Wang et al. |
| 10,584,145 | B2* | 3/2020 | Wang .................. C07J 41/0055 |
| 10,676,500 | B2 | 6/2020 | Wang et al. |
| 2005/0054559 | A1 | 3/2005 | Gallop et al. |
| 2007/0142340 | A1 | 6/2007 | Pellicciari et al. |
| 2008/0039435 | A1 | 2/2008 | Pellicciari et al. |
| 2008/0182832 | A1 | 7/2008 | Pellicciari et al. |
| 2008/0214515 | A1 | 9/2008 | Ferrari et al. |
| 2009/0062526 | A1 | 3/2009 | Yu et al. |
| 2009/0131384 | A1 | 5/2009 | Uysal et al. |
| 2009/0163474 | A1 | 6/2009 | Zhang et al. |
| 2010/0063018 | A1 | 3/2010 | Pellicciari et al. |
| 2010/0324004 | A1 | 12/2010 | McLane et al. |
| 2011/0172198 | A1 | 7/2011 | Pellicciari et al. |
| 2013/0034536 | A1 | 2/2013 | Gedulin |
| 2013/0116218 | A1 | 5/2013 | Kaplan et al. |
| 2013/0345188 | A1 | 12/2013 | Steiner et al. |
| 2014/0045808 | A1 | 2/2014 | Abel-santos et al. |
| 2014/0057886 | A1 | 2/2014 | Pellicciari et al. |
| 2014/0186438 | A1 | 7/2014 | Manku et al. |
| 2014/0187633 | A1 | 7/2014 | Manku et al. |
| 2014/0206657 | A1 | 7/2014 | Yu et al. |
| 2014/0371190 | A1 | 12/2014 | Pellicciari |
| 2015/0112089 | A1 | 4/2015 | Finch et al. |
| 2016/0130297 | A1 | 5/2016 | Xing et al. |
| 2016/0145295 | A1 | 5/2016 | He et al. |
| 2016/0145296 | A1 | 5/2016 | Wang et al. |
| 2016/0176917 | A1 | 6/2016 | Wang et al. |
| 2016/0185815 | A1 | 6/2016 | Wang et al. |
| 2016/0229886 | A1 | 8/2016 | Or et al. |
| 2016/0289262 | A1 | 10/2016 | Or et al. |
| 2017/0101434 | A1 | 4/2017 | Pellicciari et al. |
| 2017/0240585 | A1 | 8/2017 | Shen et al. |
| 2017/0240586 | A1 | 8/2017 | Or et al. |
| 2017/0240587 | A1 | 8/2017 | Or et al. |
| 2017/0260225 | A1 | 9/2017 | Pellicciari et al. |
| 2018/0148469 | A1 | 5/2018 | Wang et al. |
| 2018/0148470 | A1 | 5/2018 | Li et al. |
| 2018/0237471 | A1 | 8/2018 | Wang et al. |
| 2018/0291058 | A1 | 10/2018 | Wang et al. |
| 2019/0194245 | A1 | 6/2019 | Wang et al. |

FOREIGN PATENT DOCUMENTS

| | | | |
|---|---|---|---|
| EP | 0583566 | A2 | 2/1994 |
| EP | 1364645 | A1 | 11/2003 |
| EP | 1947108 | A1 | 7/2008 |
| JP | H1160594 | A | 3/1999 |
| JP | H11109628 | A | 4/1999 |
| KR | 20090104622 | A | 10/2009 |
| WO | 8702367 | A2 | 4/1987 |
| WO | 0037077 | A1 | 6/2000 |
| WO | 0228881 | A1 | 4/2002 |
| WO | 03030612 | A2 | 4/2003 |
| WO | 03086303 | A2 | 10/2003 |
| WO | 2005089316 | A2 | 9/2005 |
| WO | 2007089907 | A2 | 8/2007 |
| WO | 2007095174 | A2 | 8/2007 |
| WO | 2007111994 | A2 | 10/2007 |
| WO | 2008009407 | A2 | 1/2008 |
| WO | 2008091540 | A2 | 7/2008 |
| WO | 2013020108 | A2 | 2/2013 |
| WO | 2013166176 | A1 | 11/2013 |
| WO | 2013192097 | A1 | 12/2013 |
| WO | 2014036379 | A2 | 3/2014 |
| WO | 2014184271 | A1 | 11/2014 |
| WO | 2015017813 | A2 | 2/2015 |
| WO | 2015181275 | A1 | 12/2015 |
| WO | 2016073767 | A1 | 5/2016 |
| WO | 2016086169 | A1 | 6/2016 |
| WO | 2016130809 | A1 | 8/2016 |
| WO | 2016173493 | A1 | 11/2016 |
| WO | WO-2016173524 | A1 * | 11/2016 ............ C07J 43/003 |
| WO | 2016205475 | A2 | 12/2016 |
| WO | 2017027396 | A1 | 2/2017 |
| WO | 2017053826 | A1 | 3/2017 |
| WO | 2017129125 | A1 | 8/2017 |

OTHER PUBLICATIONS

"PubChem-CID-122592927, Create Date: Dec. 8, 2016".
"PubChem-CID-122592945, Create Date: Dec. 8, 2016".
Ballatore, C. et al., "Carboxylic Acid (Bio)Isosteres in Drug Design", ChemMedChem., vol. 8, No. 3, 2013, 385-395.
Briere, D. A. et al., "Novel small molecule agonist of TGR5 possesses anti-diabetic effects but causes gallbladder filling in mice", PLoS, one, vol. 10(8), 2015, 1-17.
Coleman, J. P. et al., "Metabolic Fate and Hepatocyte Toxicity of Reverse Amide Analogs of Conjugated Ursodeoxycholate in the Rat", J. Steroid Biochem. Molec. Biol., vol. 64, No. 1/2, 1998, 91-101.
Crawley, "Farnesoid X Receptor Modulators: a patent review", Expert Opinion on Therapeutic Patents, 20(8), 2010, 1047-1057.
Fini, A. et al., "Basic Cholane Derivatives. XI: Comparison between Acid and Basic Derivatives", Journal of Pharmaceutical Sciences, vol. 81, No. 7, 1992, 726-730.
Fini, et al., "Quantitative Structure-Antimicrobial Activity Relationship in 5B-Cholanyl-24-benzylamine Derivatives", Journal of Pharmaceutical Sciences, vol. 79, No. 7, 1990, 603-605.
Gioiello, A et al., "Extending SAR of bile acids as FXR ligands: discovery of 23-N-(carbocinnamyloxy)-3[alpha],7[alpha]dihydroxy-6[alpha]-ethyl-24-nor-5[beta]-ch o l an-23-amine", Bioorganic & Medicinal Chemistry, vol. 19, No. 8, Apr. 15, 2011, 2650-2658.
Griffiths, W. J. et al., "Charge-remote fragmentation of bile acids derivatized with amino-sulphonic acids", Rapid Communications in Mass Spectrometry, vol. 7, No. 3, Mar. 1, 1993, 235-240.
Honorio, K. M. et al., "Hologram QSAR Studies on Farnesoid X Receptor Activators", Letters in Drug Design & Discovery, vol. 3(4), 2006, 261-267.

(56) References Cited

OTHER PUBLICATIONS

Kim, H-S et al., "Synthesis and Antimicrobial Activity of New 3a-Hydroxy-23,24-bisnorcholane Polyamine Carbamates", Bioorganic & Medicinal Chemistry Letters, 11(23), 2001, 3065-3068.

Klinoi, J et al., "Isolation of (23r) 3a,7a,23-Trihydroxy-5b-Cholan-24-OIC . . . ", Collection Czechoslovak Chem. Commun., 51, 1986, 1722-1730.

Macchiarulo, A. et al., "Charting the chemical space of target sites: insights into the binding modes of amine and amidine groups", Journal of chemical information and modeling, 49(4):, Mar. 18, 2009, 900-912.

Macchiarulo, A. et al., "Probing the Binding Site of Bile Acids in TGR5", ACS Medicinal Chemistry Letters, 4(12), 2011, 1158-1162.

Mayorquin-Torres, M. C. et al., "application of palladium-catalyzed carboxyl anhydride-boronic acid cross coupling in the synthesis of novel bile acids analogs and modified side chains", Steroids, vol. 101, 2015, 21-27.

Meijide, F. et al., "Spontaneous Formation in the Solid State of Carbamate Derivatives of Bile Acids", Crystal Growth and Design, 11(1), 2011, 356-361.

Nikolaienko, P. V. et al., "Rapid way to fluorescent cholic-based chemosensor precursors", International Electronic Conference on Synthetic Organic Chemistry, 2011, 1-4.

Okada, J. "Preparation of bile acid derivatives and their use as nasal absorption enhancers", Database CA [Online] Chemical Abstracts Service, Columbus, Ohio, US; retrieved from STN Database accession No. 1999:142390.

Okahata, , "Base-catalyzed proton abstraction from.beta.-(p-nitrophenoxy) propiophenone in the presence of Single-chain, double-chain, and triple-chain ammonium bilayer membrane aggregates", The Chemical Society of Japan, vol. 3, Mar. 10, 1980, 442-449.

Okahata, Y. et al., "Catalytic Hydrolysis of p-Nitrophenyl Esters in the Presence of Representative Ammonium Aggregates. Specific u Activation of a Cholesteryl Nucleophile Bound to a Dialkylammonium Bilayer Membrane", Bulletin of hte Chemical Society of Japan, vol. 52(12), Dec. 1, 1979, 3647-3653.

Opsenica, I. M. et al., "4-Amino-7-chloroquinolines: Probing Ligand Efficiency Provides Botulinum Neurotoxin Serotype a Light Chain Inhibitors with Significant Antiprotozoal Activity", J. Med. Chem., vol. 56, 2013, 5860-5871.

Pellicciari, R. et al., "6α-Ethyl-Chenodeoxycholic Acid (6-ECDCA), a Potent and Selective FXR Agonist Endowed with Anticholestatic Activity", Journal of Medicinal Chemistry, 45(17), 2002, 3569-3572.

Pellicciari, R. et al., "Back Door Modulation of the Farnesoid X Receptor: Design, Synthesis and Biological Evaluation of a Series of Side Chain Modified Chenodeoxycholic Acid Derivatives", Journal of Medicinal Chem., American Chemical Society, vol. 49, No. 14, Jun. 15, 2006, 4208-4215.

Pellicciari, R. et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid", Journal of Medicinal Chemistry, American Chemical Society, vol. 47, Jul. 23, 2004, 4559-4569.

Pore, V. S. et al., "Design and synthesis of fluconazole/bile acid conjugate using click reaction", Tetrahedron, vol. 62, 2006, 11178-11186.

Roda, A. et al., "Effect of Basic Cholane Derivatives on Intestinal Cholic Acid Metabolism: In Vitro and In Vivo Activity", Journal of Pharmaceutical Sciences, vol. 81, No. 3, 1992, 237-240.

Sajisha, et al., "Remarkable isomer-selective gelation of aromatic solvents by a polymorph of a urea-linked bile acid-amino acid conjugate", RSC Advances, vol. 4(81), Abstract Only, 2014, 43167-43171.

Sato, et al., "Novel Potent and Selective Bile Acid Derivatives as TGR5 Agonists: Biological Screening, Structure-Activity Relationships, and Molecular Modeling Studies", J. Med. Chem., 51(6), 2008, 1831-1841.

Sepe, et al., "Farnesoid X receptor modulators (2011-2014): a patent review", Expert Opinion on Therapeutic Patents, 25:8, 2015, 885-896.

Solaja, B. A. et al., "Novel 4-Aminoquinolines Active against Chloroquine-Resistant and Sensitive *P. falciparum* Strains that also Inhibit Botulinum Serotype A", J. Med. Chem., vol. 51, 2008, 4388-4391.

Videnovic, M. et al., "Second Generation Steroidal 4-Aminoquinolines Are Potent, Dual-Target Inhibitors . . . ", J. Med. Chem., 57(10), Apr. 17, 2014, 4134-4153.

Willemen, H. M. et al., "Alkyl Derivatives of Cholic Acid as Organogelators: One-Component and Two-Component Gels", Langmuir, vol. 18(19), 2002, 7102-7106.

Wolff, M. E. Burger's Medicinal Chemistry and Drug Discovery, Fifth Edition, vol. 5(1): Principles and Practice published by John Wiley and Sons, 1994, 975-977.

\* cited by examiner

PROCESS FOR PREPARATION OF SULFONYLUREA BILE ACID DERIVATIVES

RELATED APPLICATIONS

This application is a divisional application of U.S. application Ser. No. 15/826,233, filed Nov. 29, 2017, now U.S. Pat. No. 10,584,145, which claims the benefit of U.S. Provisional Application No. 62/427,354 filed on Nov. 29, 2016. The entire teachings of the above applications are incorporated herein by reference.

TECHNICAL FIELD

The present invention relates to processes and intermediates useful in the preparation of biologically active molecules useful as FXR or TGR5 modulators, especially relates to bile acid derivatives and methods for their preparation and use.

BACKGROUND OF THE INVENTION

Farnesoid X Receptor (FXR) is an orphan nuclear receptor initially identified from a rat liver cDNA library (BM. Forman, et al., *Cell*, 1995, 81(5), 687-693) that is most closely related to the insect ecdysone receptor. FXR is a member of the nuclear receptor family of ligand-activated transcription factors that includes receptors for the steroid, retinoid, and thyroid hormones (DJ. Mangelsdorf, et al., *Cell*, 1995, 83(6), 841-850). The relevant physiological ligands of FXR are bile acids (D. Parks et al., *Science*, 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signaling by upregulating the expression of the cytokine Fibroblast Growth Factor (J. Holt et al., *Genes Dev.*, 2003, 17(13), 1581-1591; T. Inagaki et al., *Cell Metab.*, 2005, 2(4), 217-225).

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2008/025539, WO 2008/025540, WO 2011/020615, and WO 2013/007387.

Further small molecule FXR modulators have been recently reviewed (R. C. Buijsman et al. *Curr. Med. Chem.* 2005, 12, 1017-1075).

TGR5 receptor is a G-protein-coupled receptor that has been identified as a cell-surface receptor that is responsive to bile acids (BAs). The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm (Kawamata et al., *J. Bio. Chem.*, 2003, 278, 9435). TGR5 has been found to be identical to hGPCR19 reported by Takeda et al., *FEBS Lett.* 2002, 520, 97-101.

TGR5 is associated with the intracellular accumulation of cAMP, which is widely expressed in diverse cell types. While the activation of this membrane receptor in macrophages decreases pro-inflammatory cytokine production, (Kawamata, Y., et al., *J. Biol. Chem.* 2003, 278, 9435-9440) the stimulation of TGR5 by BAs in adipocytes and myocytes enhances energy expenditure (Watanabe, M., et al. *Nature.* 2006, 439, 484-489). This latter effect involves the cAMP-dependent induction of type 2 iodothyronine deiodinase (D2), which by, locally converting T4 into T3, gives rise to increased thyroid hormone activity. Consistent with the role of TGR5 in the control of energy metabolism, female TGR5 knock-out mice show a significant fat accumulation with body weight gain when challenged with a high fat diet, indicating that the lack of TGR5 decreases energy expenditure and elicits obesity (Maruyama, T., et al., *J. Endocrinol.* 2006, 191, 197-205). In addition and in line with the involvement of TGR5 in energy homeostasis, bile acid activation of the membrane receptor has also been reported to promote the production of glucagon-like peptide 1 (GLP-1) in murine enteroendocrine cell lines (Katsuma, S., *Biochem. Biophys. Res. Commun.*, 2005, 329, 386-390). On the basis of all the above observations, TGR5 is an attractive target for the treatment of disease e.g., obesity, diabetes and metabolic syndrome.

In addition to the use of TGR5 agonists for the treatment and prevention of metabolic diseases, compounds that modulate TGR5 modulators are also useful for the treatment of other diseases e.g., central nervous diseases as well as inflammatory diseases (WO 01/77325 and WO 02/84286). Modulators of TGR5 also provide methods of regulating bile acid and cholesterol homeostasis, fatty acid absorption, and protein and carbohydrate digestion.

There is a need for the development of FXR and/or TGR5 modulators for the treatment and prevention of disease. The present invention has identified compounds, which contain an amino, urea, sulfonyurea or sulfonamide moieties, which modulate FXR and/or TGR as well as methods of using these compounds to treat disease.

SUMMARY OF THE INVENTION

The present invention relates to processes for preparing a compound of Formula (I):

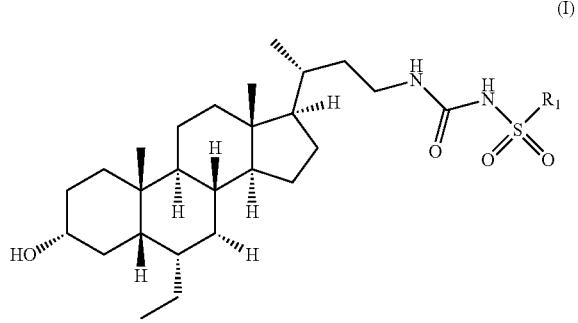

or a pharmaceutically acceptable salt or solvate thereof, wherein

R₁ is selected from the group consisting of:

1) substituted or unsubstituted —C₁-C₈ alkyl;
2) substituted or unsubstituted —C₂-C₈ alkenyl;
3) substituted or unsubstituted —C₂-C₈ alkynyl;
4) substituted or unsubstituted —C₃-C₈ cycloalkyl;
5) substituted or unsubstituted aryl;
6) substituted or unsubstituted arylalkyl;
7) substituted or unsubstituted 3- to 12-membered heterocycloalkyl;
8) substituted or unsubstituted heteroaryl;
9) substituted or unsubstituted heteroarylalkyl; and
10) NR₂R₃; wherein, R₂ and R₃ are each independently selected from hydrogen, substituted or unsubstituted —C₁-C₈ alkyl, substituted or unsubstituted —C₂-C₈ alkenyl, substituted or unsubstituted —C₂-C₈ alkynyl, substituted or unsubstituted —C₃-C₈ cycloalkyl. Alternatively R₂ and R₃ are taken together with the nitrogen atom to which they attached to form an optionally substituted 3- to 12-memebered hetercyclic ring.

A preferred embodiment of a compound of Formula (I) is the compound (III):

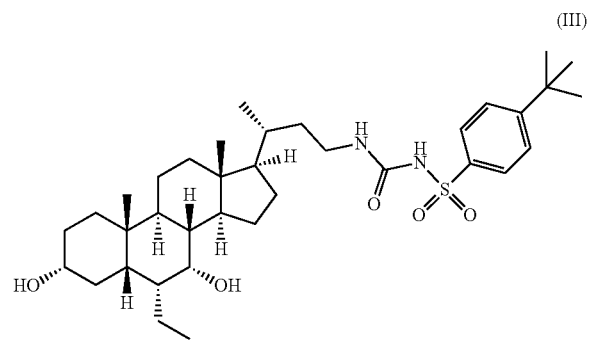

In certain embodiments, the present invention relates to a method of preparing a dialkylammonium salt of compound (III).

In certain embodiment, the present invention relates to a process for preparing a crystalline form of a dialkylammonium salt of a compound (III).

In certain embodiments, the present invention relates to a process for preparing a solid amorphous form of the compound (III) by dissolving compound (III) in a polar solvent, such as, but not limited to, methanol, ethanol, isopropyl acetate, acetone, ethyl acetate, acetonitrile, then mixing the resulting solution with an antisolvent, such as, but not limited to, water, or a miscible nonpolar solvent, such as hexane, or heptane, to precipitate the amorphous form. Preferably, compound (III) is dissolved in methanol, and then the methanol solution is added to water to precipitate the amorphous form of compound (III).

In certain embodiments, the present invention relates to methods of preparing a compound (II) and salts and derivatives thereof which are useful intermediates in the synthesis of biologically active molecules, including compounds of Formula (I).

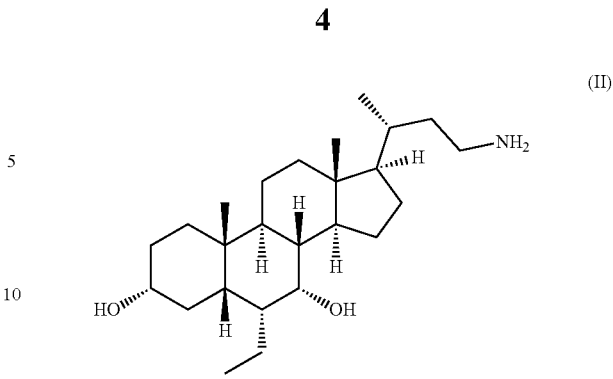

The invention further relates to methods for increasing product yield and decreasing process steps for intermediate and large scale production of compounds of Formula (I), Compound (II), and Compound (III).

The compounds of Formulas (I) and compound (III) are useful for the treatment of a chronic liver disease, such as a disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency. See, for example WO2016/086218, which is incorporated herein by reference in its entirety.

BRIEF SUMMARY OF THE DRAWINGS

FIG. 6 presents the ¹H-NMR spectrum (in CDCl₃) of compound 12 as prepared in Example 9a.

FIG. 7 presents the ¹H-NMR spectrum (in CDCl₃) of compound (III) as prepared in Example 10a.

DETAILED DESCRIPTION OF THE INVENTION

Figure 1:
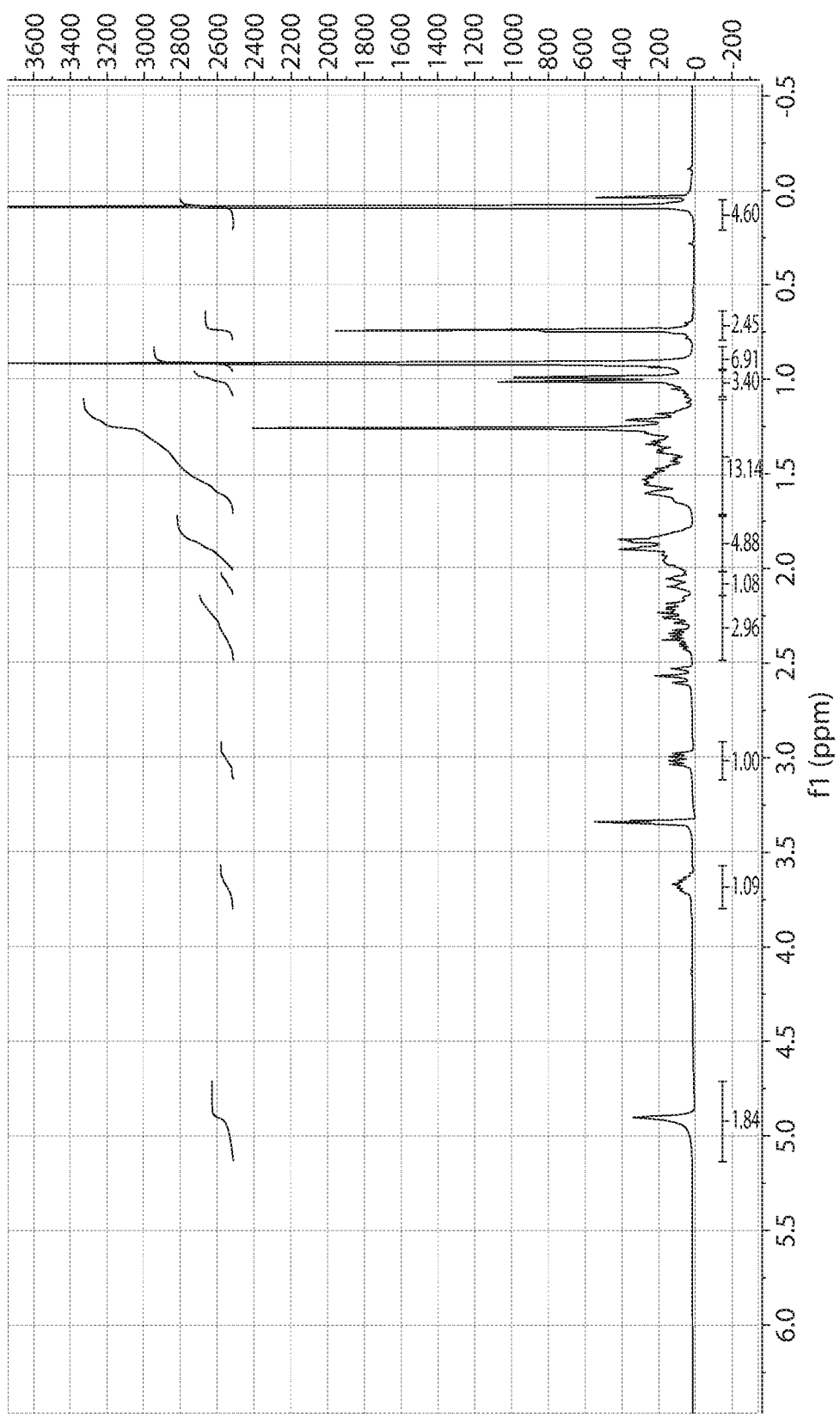
FIG. 1 presents the ¹H-NMR spectrum (in CD₃OD) of compound 2-E, as prepared in Example 1.
Figure 2:
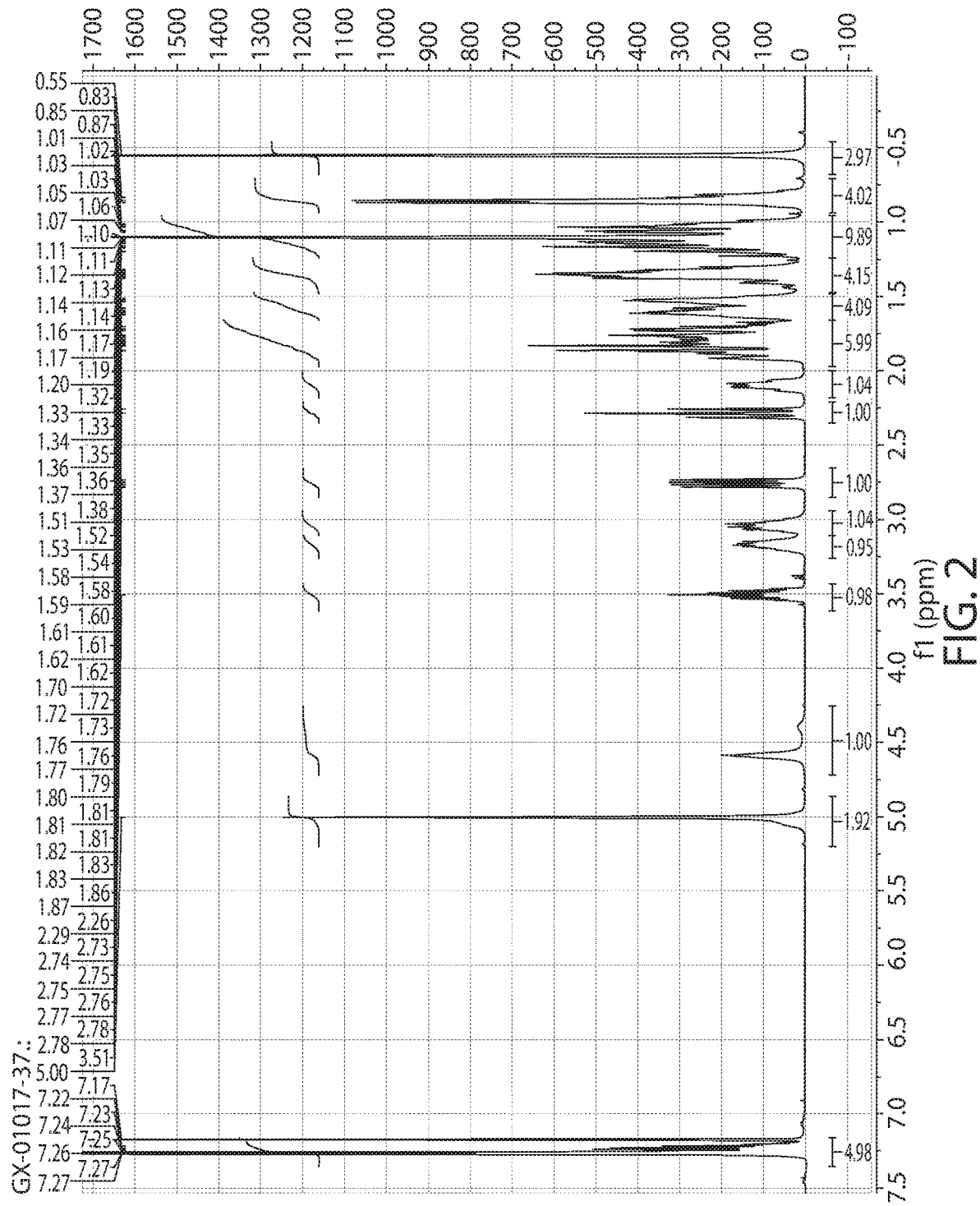
FIG. 2 presents the ¹H-NMR spectrum (in CDCl₃) of compound 4-E as prepared in Example 3.
Figure 3:
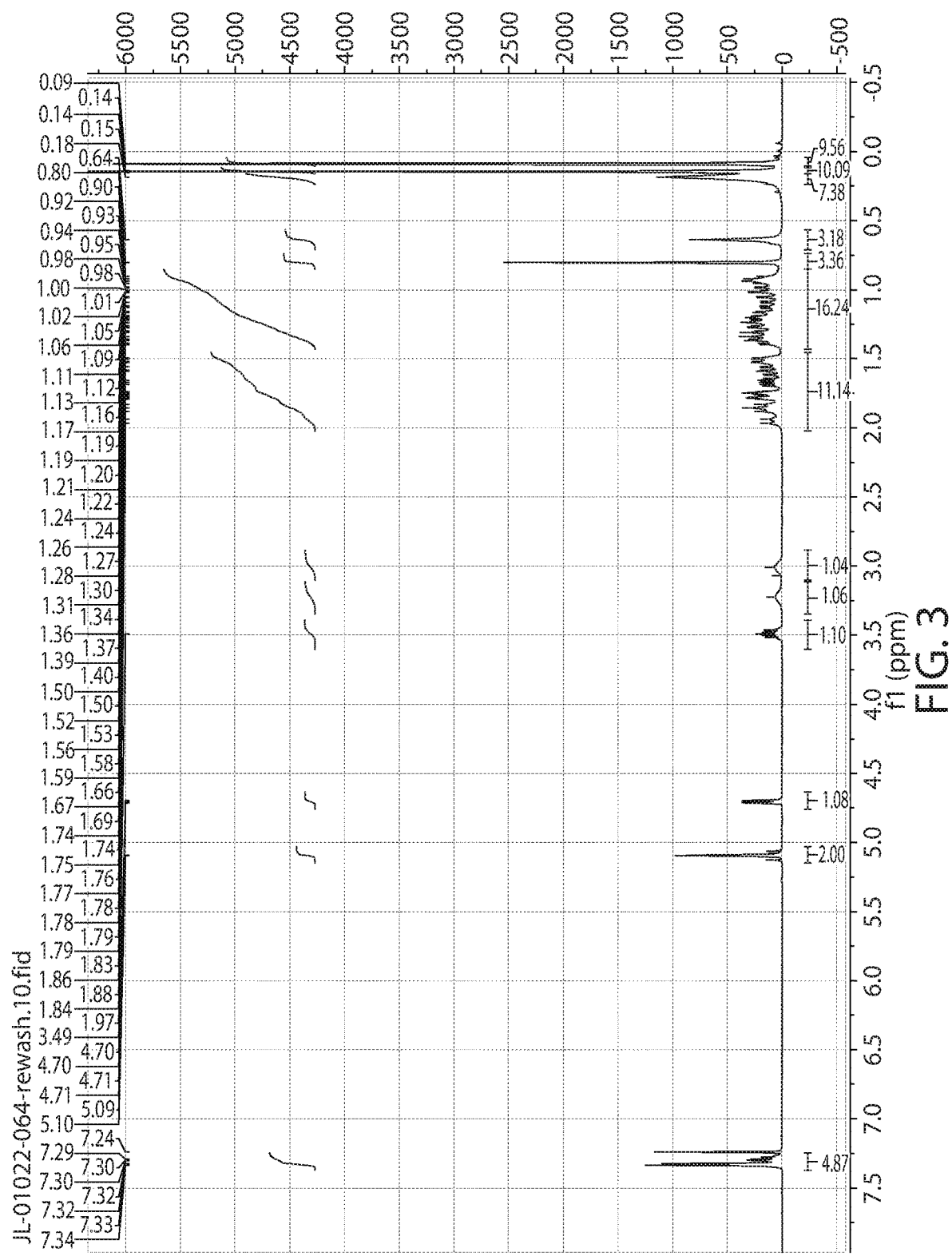
FIG. 3 presents the ¹H-NMR spectrum (in CDCl₃) of compound 5-E as prepared in Example 4.
Figure 4:
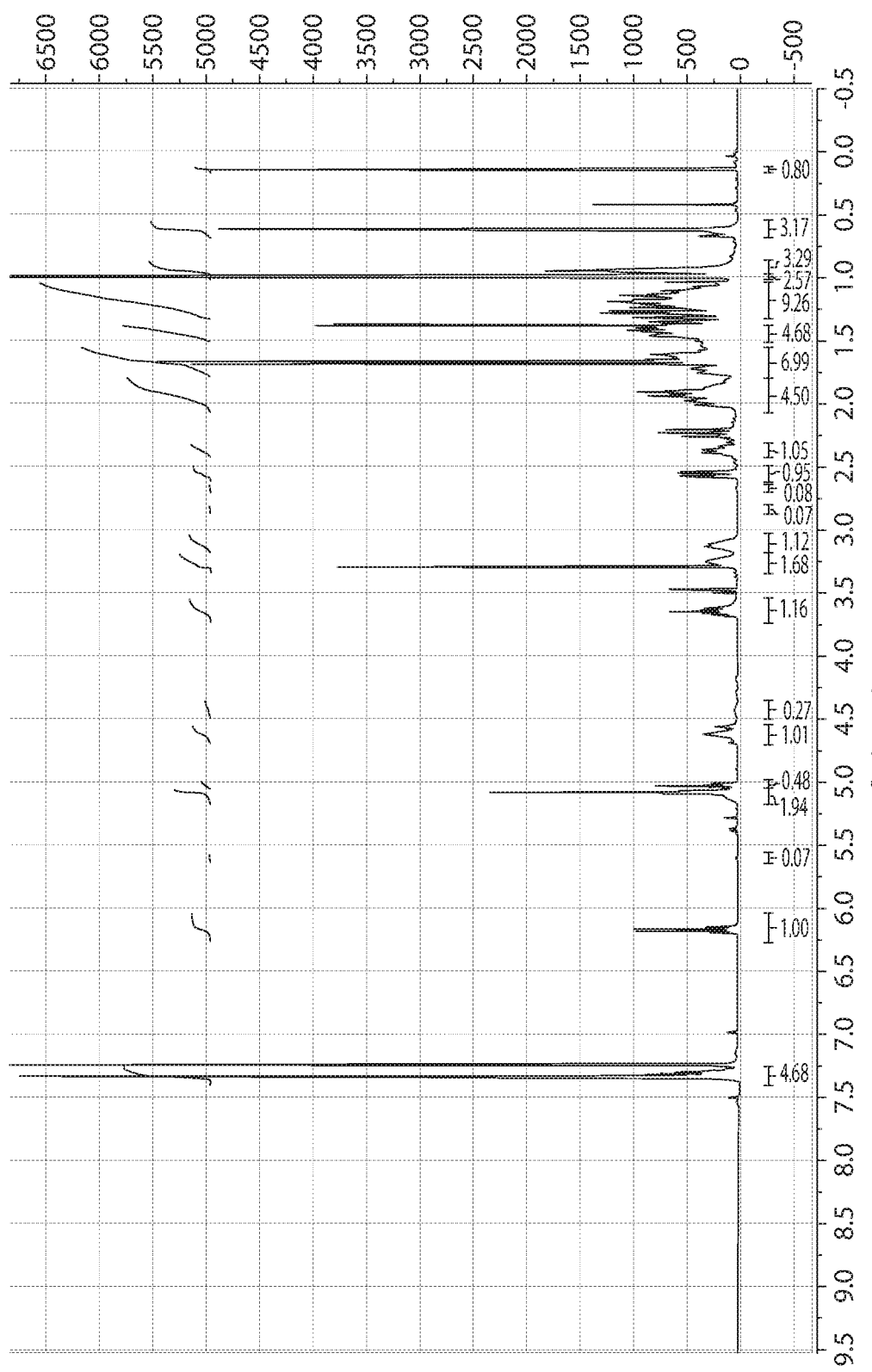
FIG. 4 presents the ¹H-NMR spectrum of compound 6-E (in CDCl₃) as prepared in Example 5.
Figure 5:
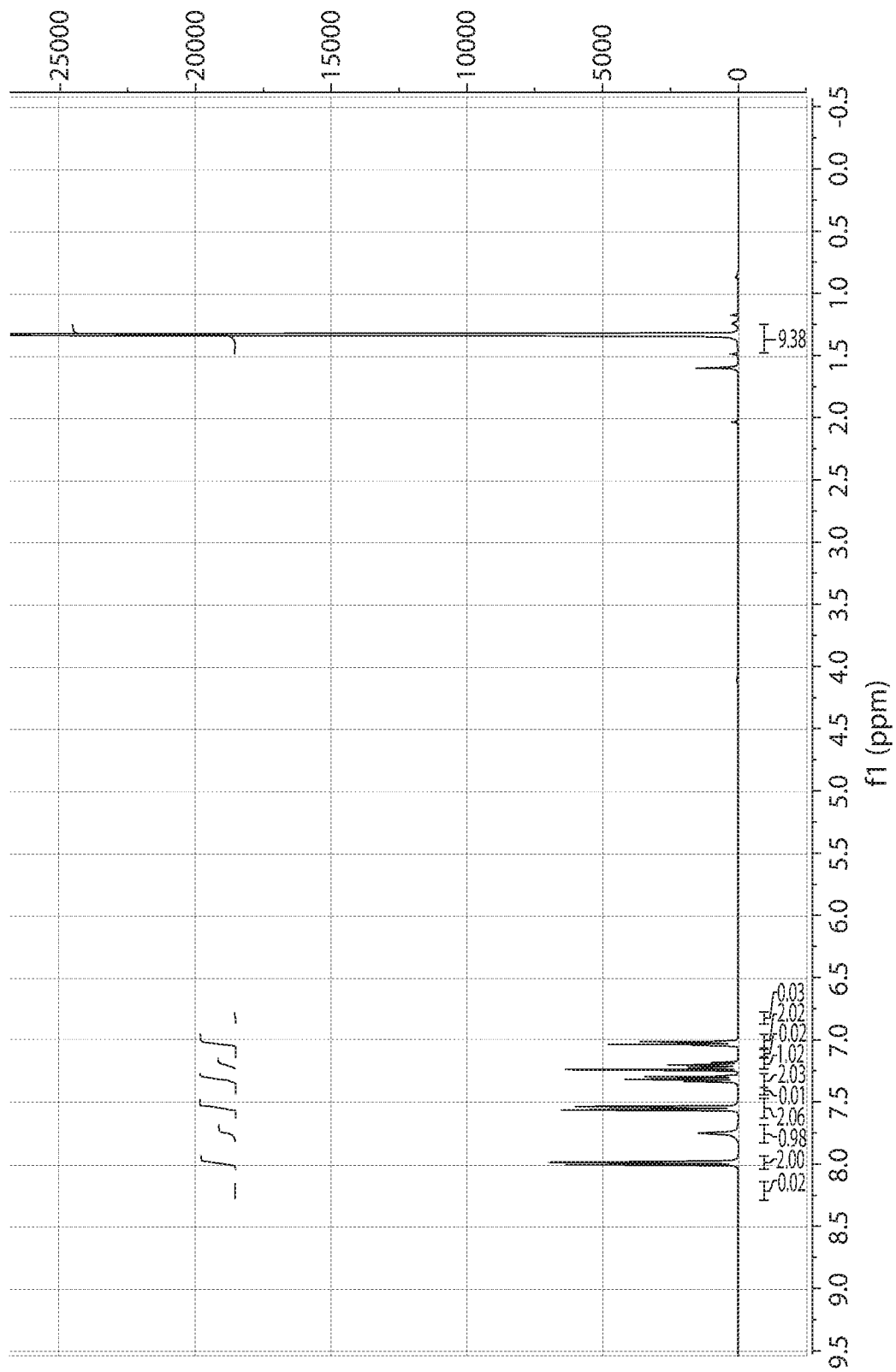
FIG. 5 presents the ¹H-NMR spectrum (in CDCl₃) of compound 10D as prepared in Example 7.
Figure 6:
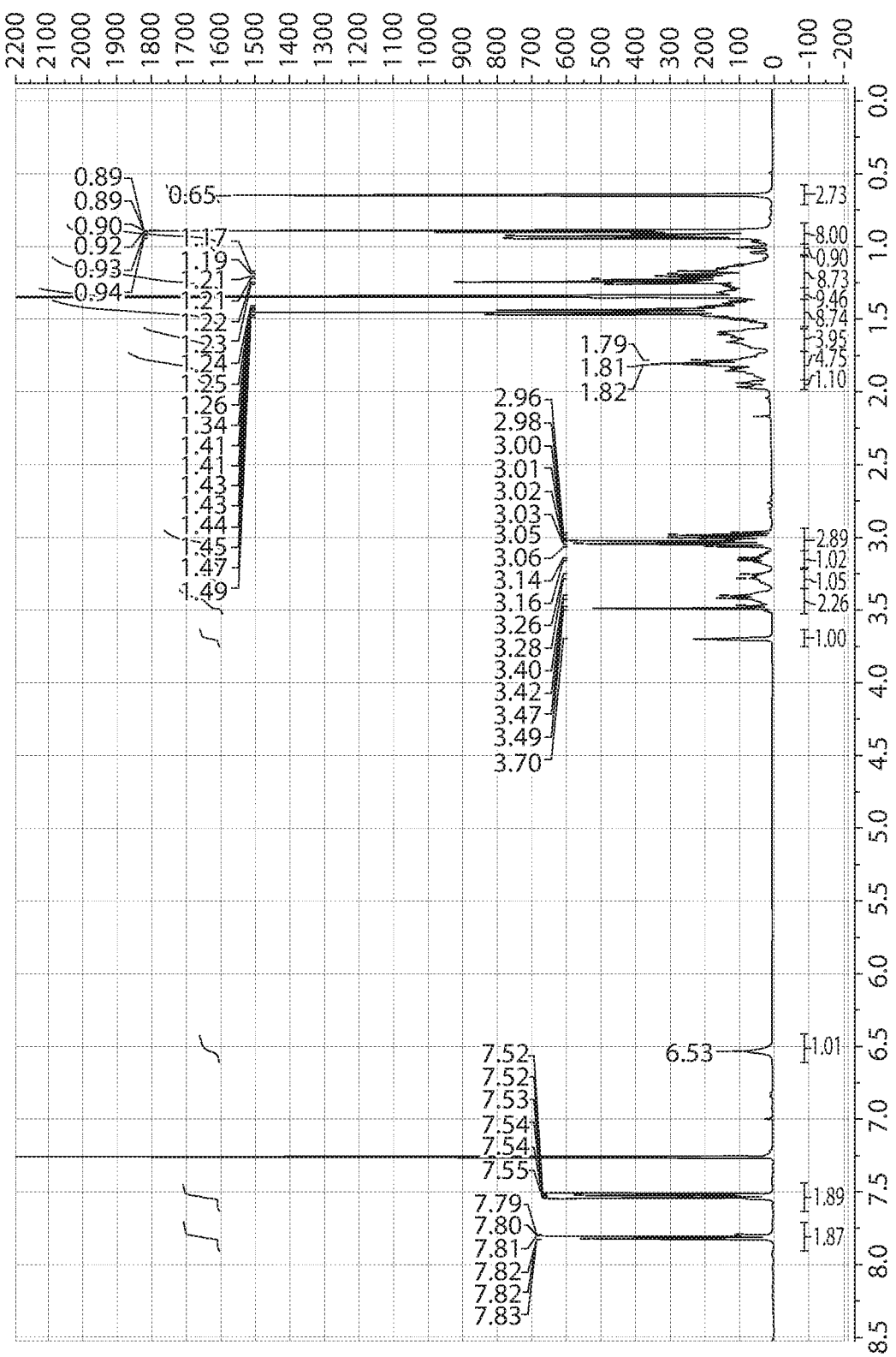
Figure 7:
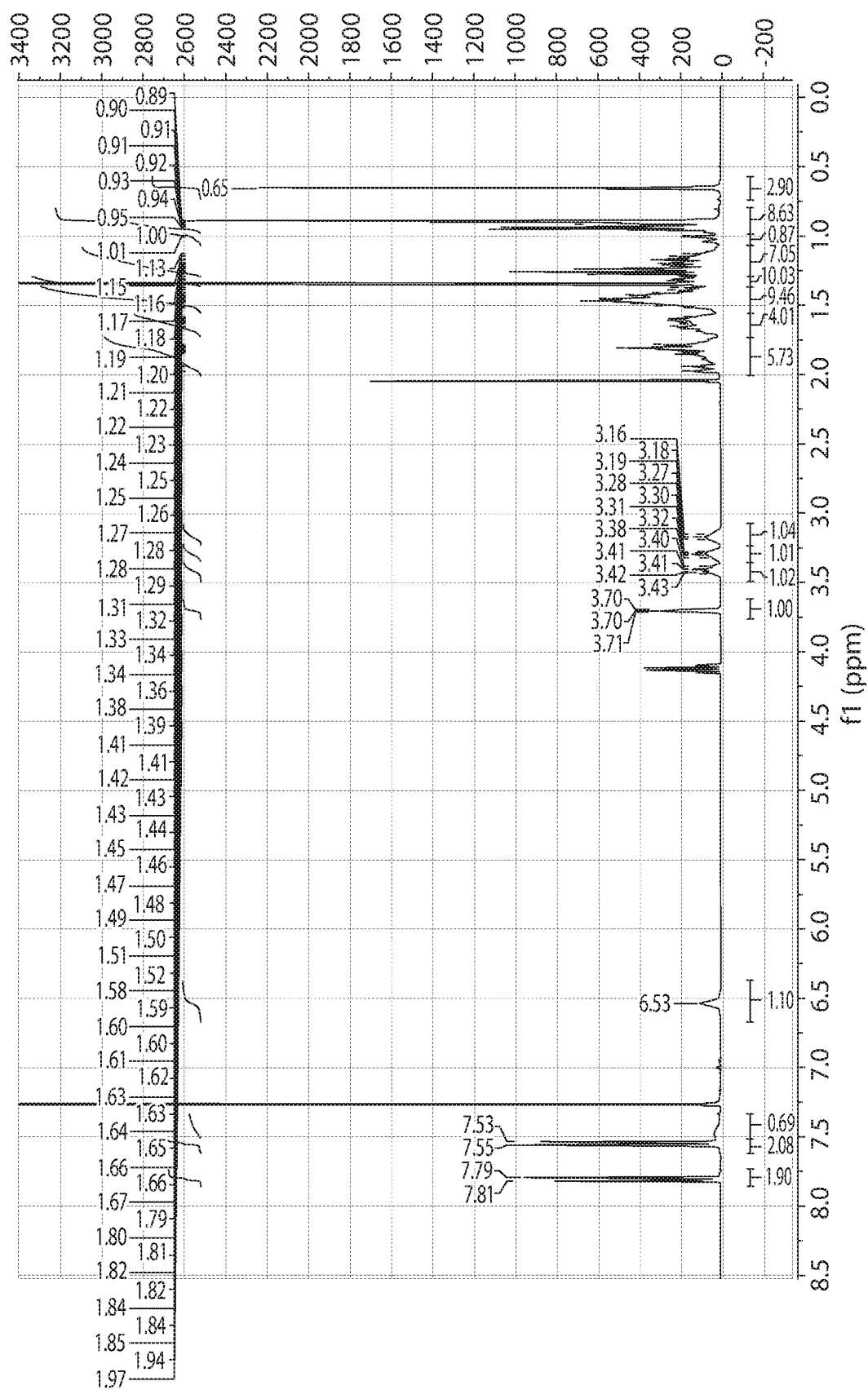
Figure 8:
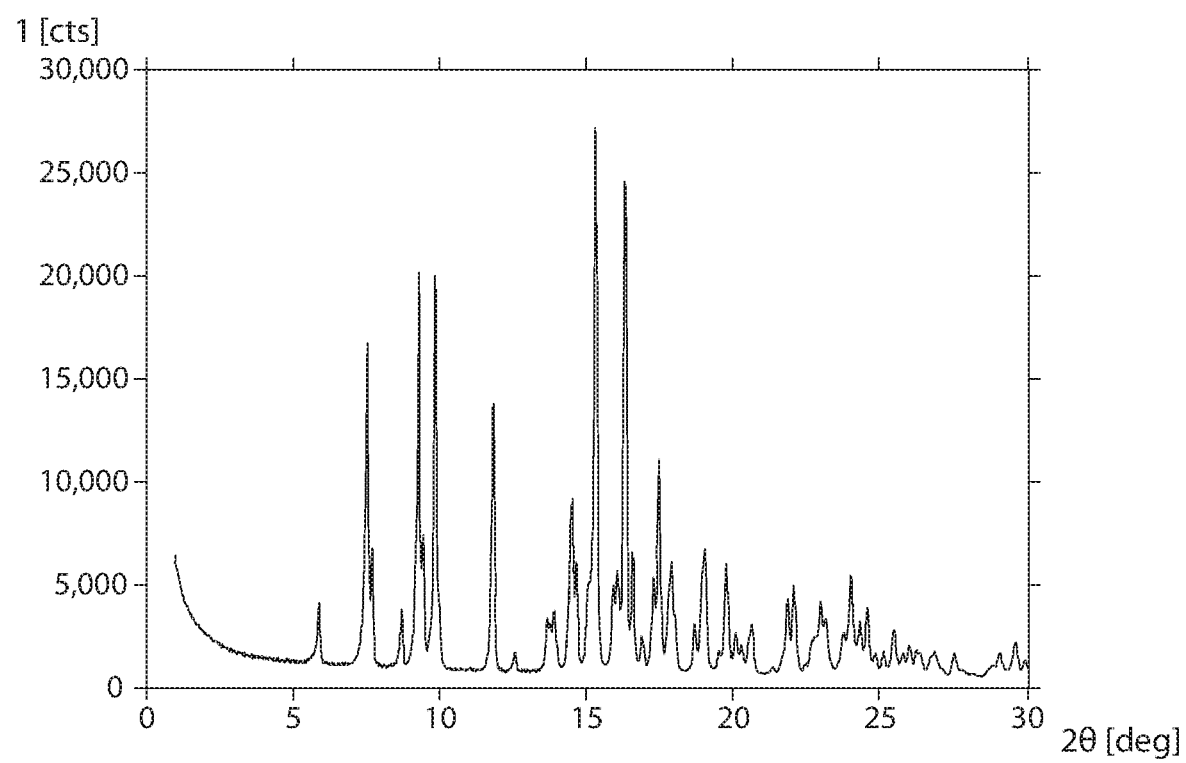
FIG. 8 presents the XRPD pattern of compound 12 recrystallized from acetone as in Example 9b.
Figure 9:
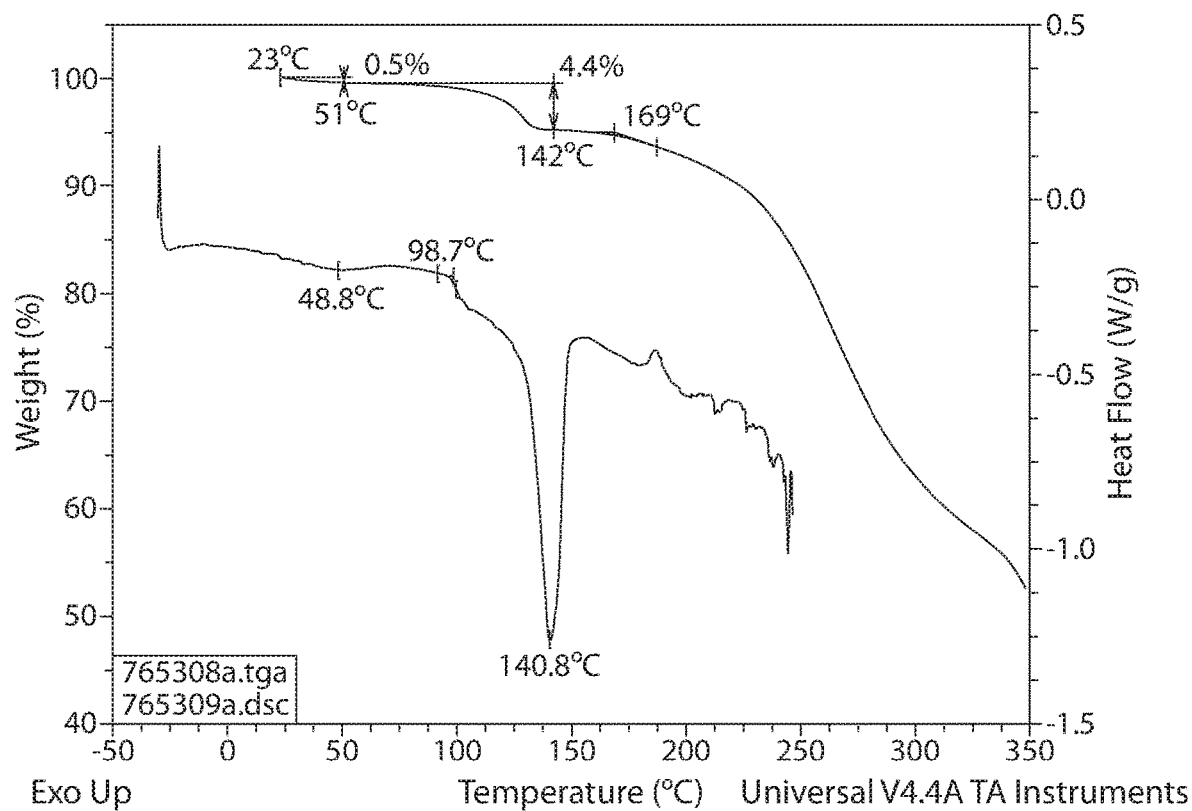
FIG. 9 presents the TGA and DSC thermograms of compound 12 recrystallized from acetone as in Example 9b.
Figure 10:
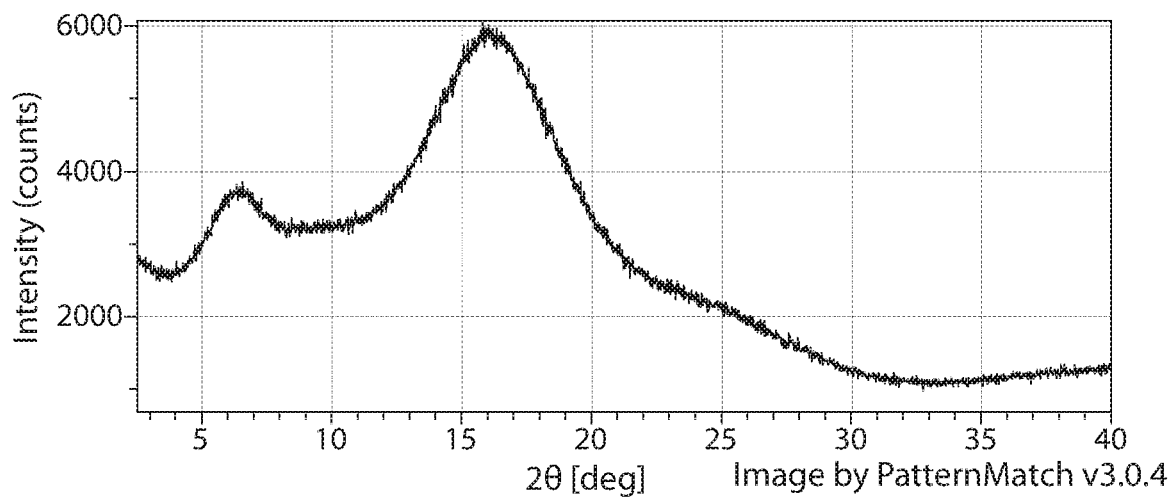
FIG. 10 presents the XRPD pattern of compound (III) precipitated from methanol as in Example 10b.

The present invention relates to processes for preparing a compound of Formula (I)

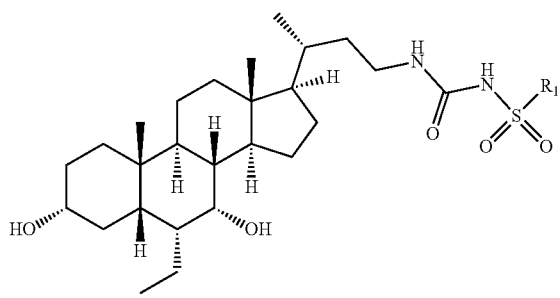

or a pharmaceutically acceptable salt or solvate thereof, wherein $R_1$ is as defined previously.

The present invention also relates to a process for preparing the compound (II) and its salts and derivatives. Such compounds are useful intermediates in the synthesis of biologically active molecules,

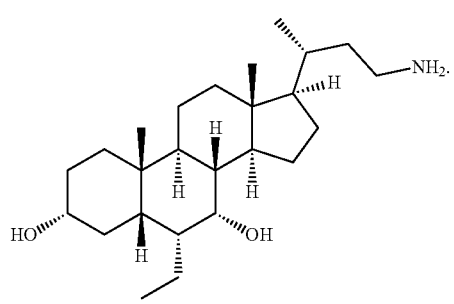

In another embodiment, the present invention relates to processes for preparing the compound (III), (III)

In yet another embodiment, the present invention relates to processes for preparing a crystalline form of compound (III) diethylammonium salt.

In yet another embodiment, the present invention relates to processes for preparing an amorphous form of compound (III).

In one embodiment, the invention provides a method for preparing a compound (II) as set forth in scheme 1. The method comprises the steps of (1) protecting the hydroxyl group of 7-keto lithocholic acid (KLCA, compound 1) to produce compound 2; (2) reacting compound 2 with an azide source in the presence of benzyl alcohol or a substituted benzyl alcohol to produce compound 3; (3) deprotecting compound 3 to produce compound 4; (4) reacting compound 4 with a silylating agent in the presence of a base to produce compound 5; (5) reacting compound 5 with acetaldehyde to produce compound 6; (6) hydrogenating compound 6 to produce compound 7; (7) reacting compound 7 with base in a protic solvent or a mixture of a protic solvent and a non-protic solvent to produce compound 8; (8) reducing compound 8 to produce the compound (II). As shown in scheme 1, the compound (II) can be converted to an acid addition salt by reaction with an acid HA. HA is preferably a pharmaceutically acceptable acid, such as HCl.

Scheme 1

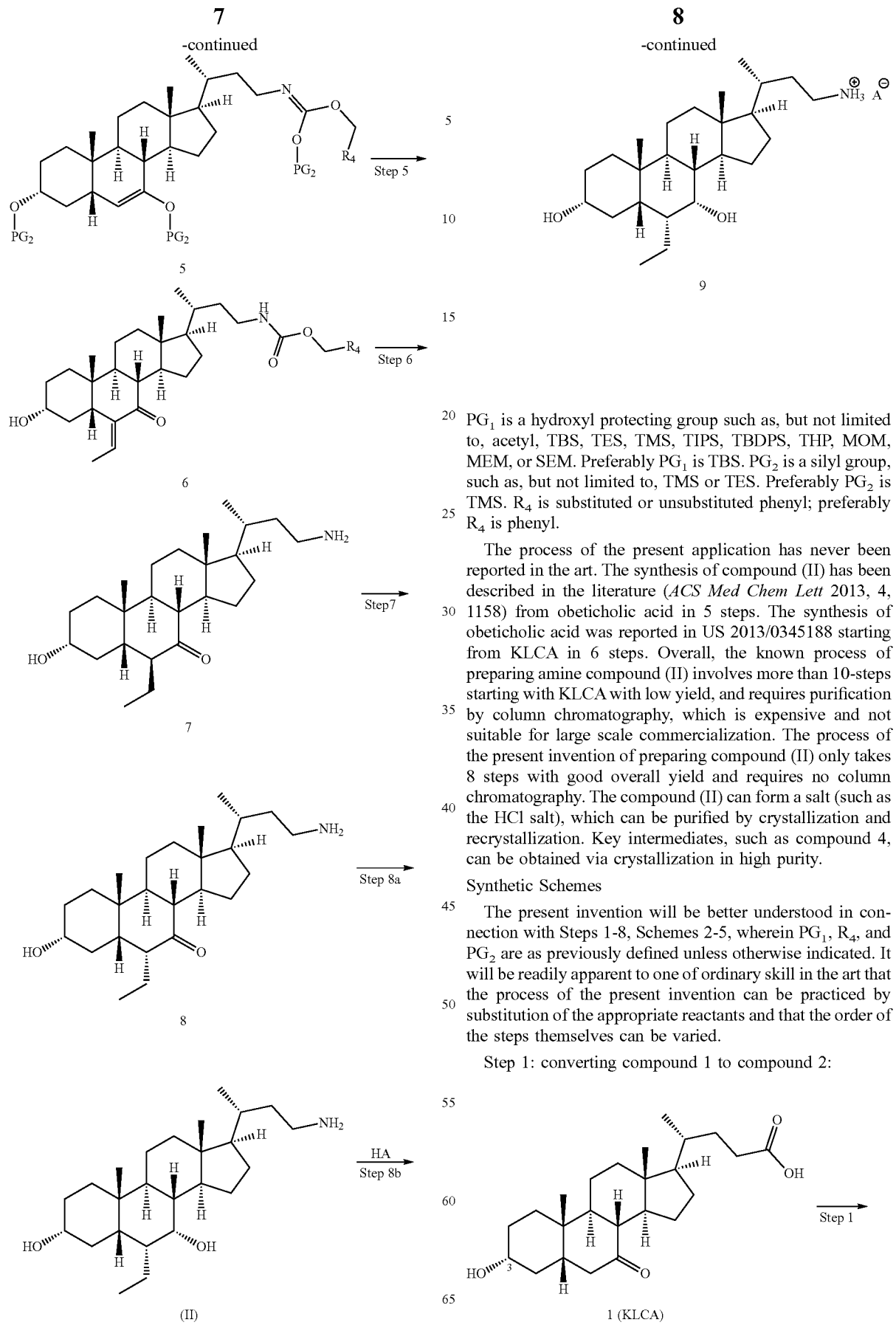

PG$_1$ is a hydroxyl protecting group such as, but not limited to, acetyl, TBS, TES, TMS, TIPS, TBDPS, THP, MOM, MEM, or SEM. Preferably PG$_1$ is TBS. PG$_2$ is a silyl group, such as, but not limited to, TMS or TES. Preferably PG$_2$ is TMS. R$_4$ is substituted or unsubstituted phenyl; preferably R$_4$ is phenyl.

The process of the present application has never been reported in the art. The synthesis of compound (II) has been described in the literature (*ACS Med Chem Lett* 2013, 4, 1158) from obeticholic acid in 5 steps. The synthesis of obeticholic acid was reported in US 2013/0345188 starting from KLCA in 6 steps. Overall, the known process of preparing amine compound (II) involves more than 10-steps starting with KLCA with low yield, and requires purification by column chromatography, which is expensive and not suitable for large scale commercialization. The process of the present invention of preparing compound (II) only takes 8 steps with good overall yield and requires no column chromatography. The compound (II) can form a salt (such as the HCl salt), which can be purified by crystallization and recrystallization. Key intermediates, such as compound 4, can be obtained via crystallization in high purity.

Synthetic Schemes

The present invention will be better understood in connection with Steps 1-8, Schemes 2-5, wherein PG$_1$, R$_4$, and PG$_2$ are as previously defined unless otherwise indicated. It will be readily apparent to one of ordinary skill in the art that the process of the present invention can be practiced by substitution of the appropriate reactants and that the order of the steps themselves can be varied.

Step 1: converting compound 1 to compound 2:

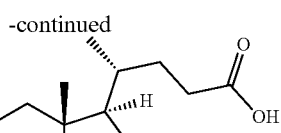

2

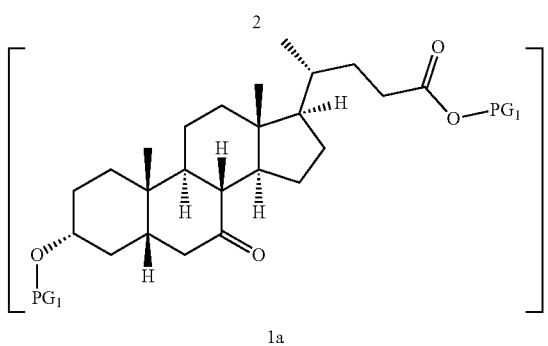

1a

Compound 1, 3α-hydroxy-7-keto-5β-cholan-24-oic acid (KLCA) can be prepared in large scale from CDCA following the literature procedures, for example the procedures described in *Organic Process Research & Development,* 6(5), 665-669; 2002.

Step 1 is the protection of the 3-hydroxyl group of KLCA with a suitable hydroxyl protecting group $PG_1$, which can be, but is not limited to, acetyl, TBS, TES, TMS, TIPS, TBDPS, THP, MOM, MEM, and SEM. Preferably $PG_1$ is t-butyldimethyl silyl (TBS). In step 1, KLCA is reacted with a reagent $PG_1$-X, wherein X is a leaving group, preferably Cl, Br, I or OTf, in the presence of a base such as, but not limited to, imidazole, TEA, DIPEA. The preferred base is imidazole. The KCLA is preferably reacted with a stoichiometric or excess amount of the hydroxyl protection reagent, such as, but not limited to 2 to 2.5 eq., for example, 2 eq., 2.2 eq., or 2.5 eq., to generate the 3,24-bis-O-$PG_1$ intermediate of formula (1a), which is treated with an alcohol, such as, but not limited to MeOH, and an inorganic base such as, but not limited to, $K_2CO_3$, to yield compound 2. In one aspect, the 3,24-bis-O-$PG_1$ intermediate, compound 1a, is isolated and then converted to compound 2. In a preferred aspect, compound 1a, is not isolated and is directly converted to compound 2.

Step 2: converting compound 2 to compound 3:

Step 2

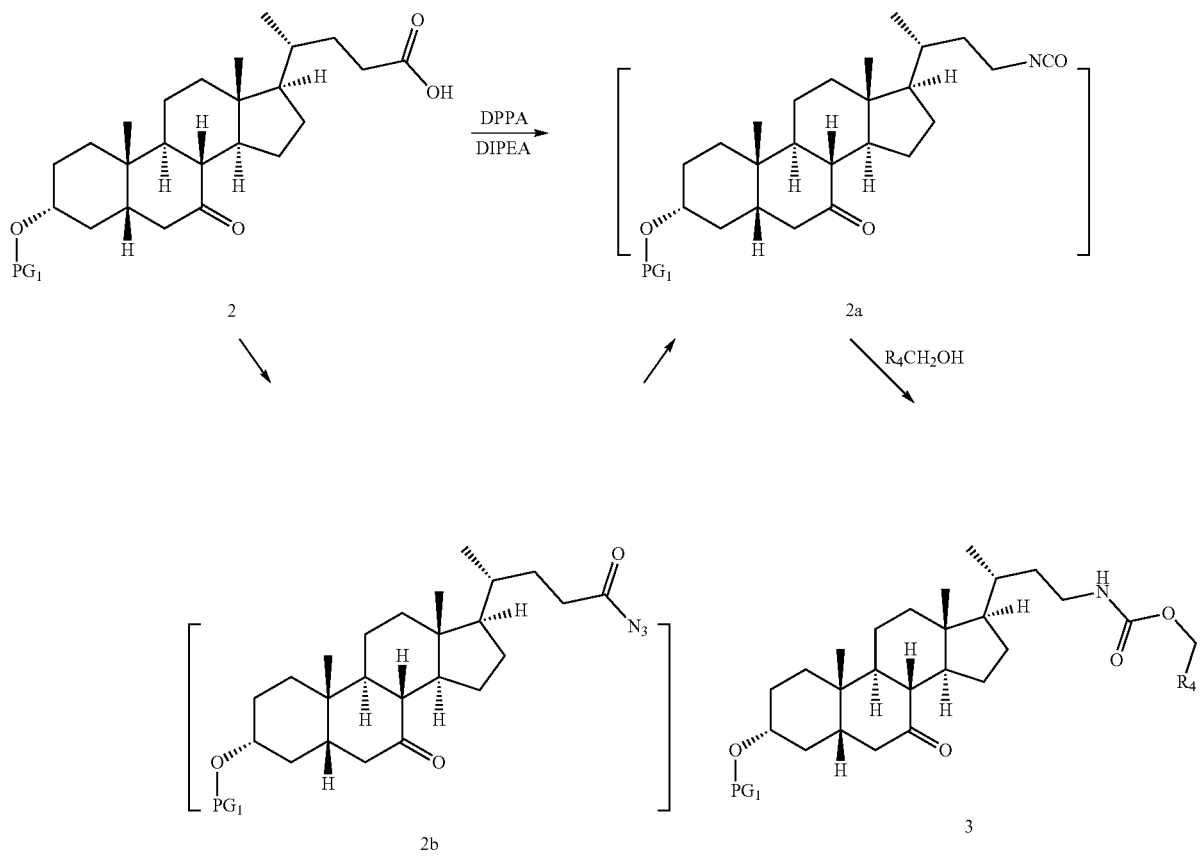

Step 2 is the conversion of compound 2 to compound 3 via a Curtius rearrangement which generates the intermediate isocyanate compound 2a. In one aspect, the isocyanate intermediate 2a is directly generated in situ by reacting compound 2 with a suitable acylazide formation reagent, such as, but not limited to, DPPA in the presence of a organic base, such as, but not limited to, DIPEA or TEA, at an elevated temperature. The preferred organic base is DIPEA. In one aspect, the elevated temperature is from 50° C. to 120° C. In one aspect, the temperature is from 60° C. to 110° C. In one aspect, the temperature is from 80 to 90° C. In another aspect, the isocyanate intermediate 2a is generated by converting the carboxylic group of compound 2 to an acyl azide intermediate 2b first at a lower temperature, such as from −10° C. to 25° C., via acyl azide synthesis procedures known in the art, and then the acyl azide intermediate 2b is converted to the isocyanate intermediate 2a upon heating at an elevated temperature, such as 50° C. to 120° C. The isocyanate intermediate 2a reacts with benzyl alcohol or substituted benzyl alcohol $R_4CH_2OH$ to give compound 3. In one aspect of Step 2, the isocyanate intermediate 2a is isolated before reacting with $R_4CH_2OH$. In one preferred aspect, the isocyante intermediate 2a is generated in situ and the crude product is reacted with $R_4CH_2OH$ to give the compound 3 directly.

Step 3: converting compound 3 to compound 4:

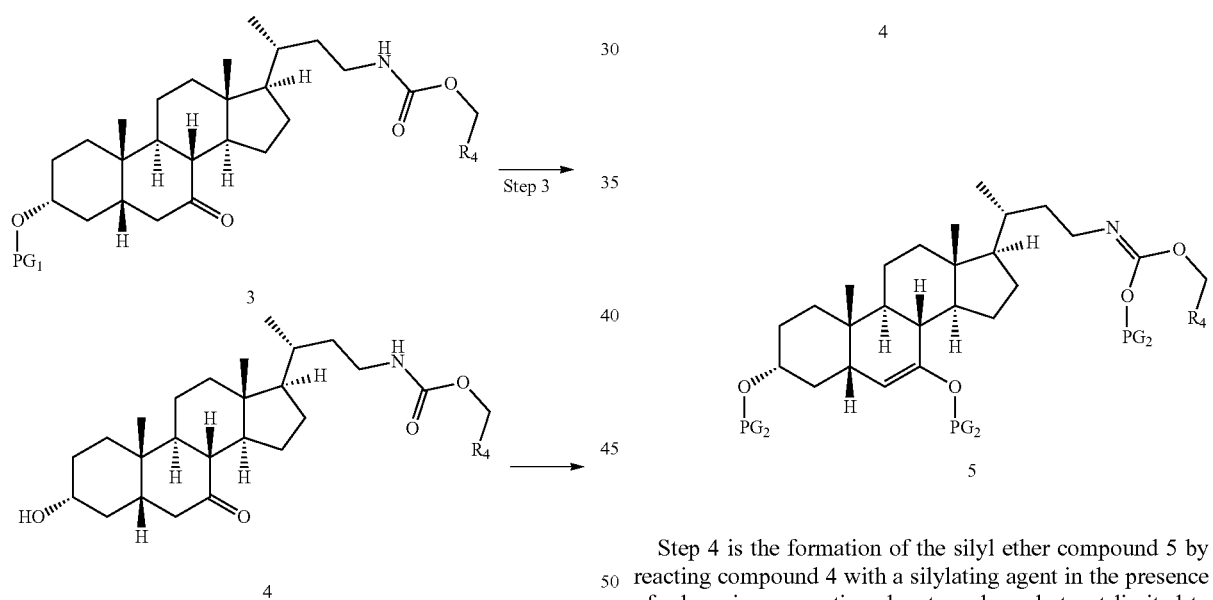

Step 3 is the removal of the protecting group, $PG_1$ of compound 3 to form compound 4. The protecting group can be removed under suitable deprotection conditions as are known in the art. For example, when $PG_1$ is a silyl group, it can be removed by a deprotecting reagent such as, but not limited to, TBAF, or an acid such as HCl. Preferably compound 3 is treated with an acid in a protic solvent. In one aspect of Step 3, compound 3 from Step 2 is used directly without further purification. Preferably compound 3 is treated with an acid, such as HCl, in a protic solvent such as, but not limited to, MeOH, EtOH, iPrOH, $H_2O$, or a mixture of two or more of these solvents, or a mixture of above protic solvent(s) with an aprotic solvent(s) such as, but not limited to, THF, DCM, EtOAc, acetonitrile, or toluene. In a preferred aspect, the solvent is MeOH. In another preferred aspect, the solvent is EtOH. The reaction can be carried out at a temperature ranging from −10° C. to 50° C. In a preferred aspect, the reaction temperature is from 0° C. to 30° C. In another preferred aspect, the reaction temperature is about 25° C. In yet another preferred aspect, compound 3 is treated with HCl in MeOH at room temperature to give compound 4. Compound 4 can be crystallized from MeOH to provide compound 4 with purity greater than 85%. In one aspect, the purity of obtained compound 4 is greater than 90%. In one aspect, the purity of obtained compound 4 is greater than 95%.

The overall yield for the conversion of compound 2 to compound 4 is greater than 60% after the recrystallization of compound 4 in two steps.

Step 4: converting compound 4 to compound 5:

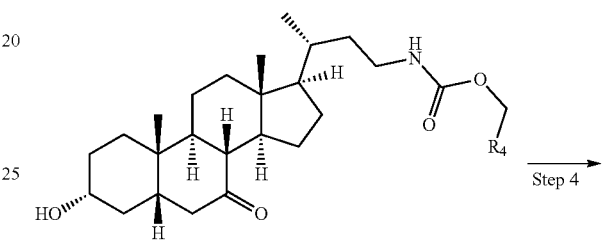

Step 4 is the formation of the silyl ether compound 5 by reacting compound 4 with a silylating agent in the presence of a base in an aprotic solvent, such as, but not limited to DCM and THF.

In one aspect of Step 4, the silylating agent is TMSCl, and the base is a strong organic base such as, but not limited to, NaHMDS, LiHMDS or LDA, and the reaction occurs at a lower temperature, such as about −78° C.

In another preferred aspect of Step 4, TMSOTf is the silylating agent and is used together with an organic base such as, but not limited to, TEA or DIPEA at a reaction temperature ranging from −20° C. to 30° C. In a preferred aspect, the reaction temperature is from about −5° C. to about 15° C. In another aspect, the temperature is about 0° C. The molar ratio of TMSOTf to compound 4 preferably ranges from 3 to 12. In one aspect, the molar ratio is 3 to 6. In one aspect, the molar ratio is 4.5 to 5.5.

Step 5: converting compound 5 to compound 6:

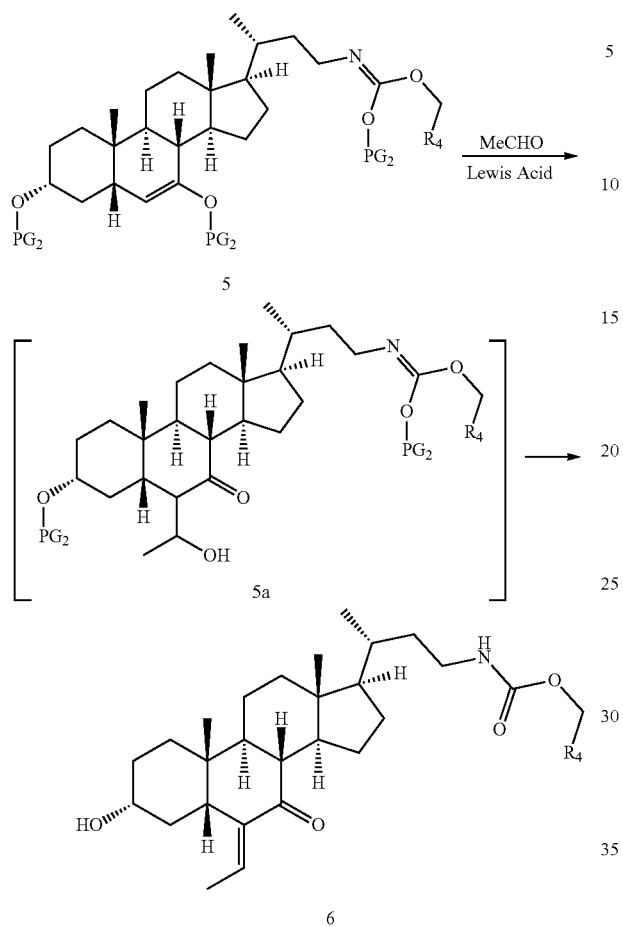

Step 5 is an Aldol reaction of compound 5 with acetaldehyde to produce intermediate compound 5a, followed by elimination to form compound 6 in the presence of a Lewis acid, such as, but not limited to, a BF$_3$ reagent, or Ti(OiPr)$_4$. In one aspect of Step 5, the Lewis acid is an adduct of BF$_3$, such as BF$_3$-Et$_2$O. The reaction is carried out in an aprotic solvent, such as, but not limited to, DCM. The reaction temperature is preferably from about −78° C. to room temperature (about 25° C.). In one aspect, the reaction temperature is from about −78° C. to about −50° C. In another preferred aspect, the reaction temperature is about −60° C.

Prior to conducting Step 5, it is preferred to remove the residual water in the crude compound 5 from Step 4 to control the decomposition of compound 5. In one aspect, compound 5 produced in step 4 is dissolved in an aprotic solvent, such as, but not limited to, DCM, heptane, hexanes, or toluene, and is washed extensively with water to remove trace amount of the base. The water content is preferably limited to <0.5% (Karl Fisher titration) by co-distillation with an anhydrous aprotic solvent, such as DCM, hexane, heptane, toluene, or THF.

Following the reaction of compound 5 with acetaldehyde at about −78° C. to about −50° C., the Aldol product compound 5a is formed initially as the major product. Methanol is then added to the reaction mixture to quench the reaction and facilitate the elimination to form the olefin compound 6. Alternatively the reaction is allowed to proceed at a higher temperature, such as from −10° C. to room temperature, without the addition of methanol to facilitate the olefin formation to provide compound 6.

In one aspect of Step 5, compound 6 is a mixture of E- and Z-olefin isomers as illustrated by the structures of compound 6A below. The E/Z ratio can be 1/1 to >9/1.

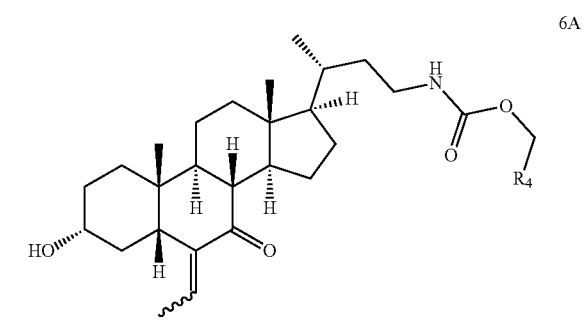

In one aspect of Step 5, E-isomer compound 6 is obtained as the dominant isomer (E-isomer 6 is greater than 80% and Z-isomer is less than 20%). In another aspect, the E-isomer is greater than 90% and Z-isomer is less than 10%. In another aspect, the E-isomer is greater than 95% and Z-isomer is less than 5%.

In one aspect of Step 5, the crude product 6 contains less than 5% of ketone compound 3. In another aspect, the crude product 6 contains less than 3% of ketone compound 3. In another aspect, the crude product 6 contains less than 2% of ketone compound 3.

Step 6: converting compound 6 to compound 7:

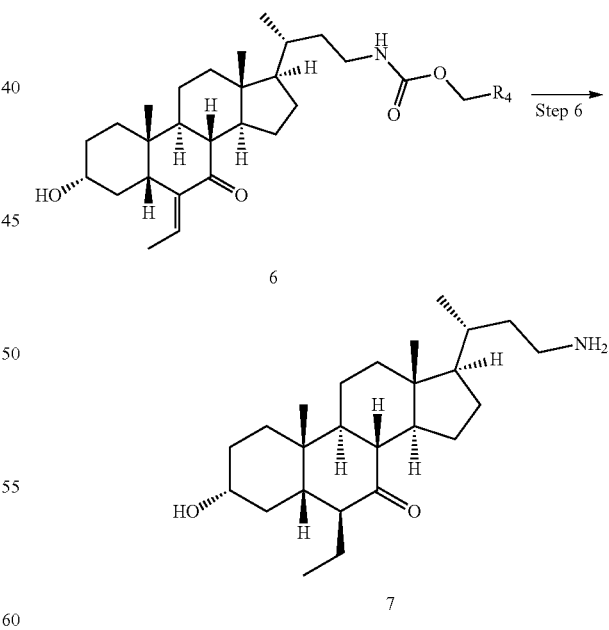

In Step 6, compound 6 from Step 5 is converted to compound 7 via a catalytic hydrogenation to remove benzyl carbamate protecting group and to reduce olefin in one step. In one aspect of Step 6, the crude product 6 obtained after work-up of step 5 is used directly without purification. In one aspect of Step 6, crude product 6 contains both E- and Z olefin isomers (6A). The percentage of Z-isomer preferably ranges from 0% to 50%.

The catalytic hydrogenation is carried out in the presence of a catalyst such as, but not limited to, palladium on carbon (Pd/C), Pd(OAc)$_2$, Pd(OH)$_2$ and PtO$_2$. The preferred catalyst is Pd/C. The palladium content of this Pd/C can range from about 5% to about 10%. The amount of catalyst can range from about 1 mol % to about 10 mol %. The hydrogen source can be, but is not limited to, hydrogen gas and ammonium formate. The pressure of hydrogen gas preferably ranges from atmosphere pressure to about 500 psi. In one aspect of Step 6, the pressure of hydrogen gas is the atmosphere pressure. In one aspect of Step 6, the pressure of hydrogen gas is from about 50 to about 150 psi. The reaction temperature of Step 6 preferably ranges from about 5° C. to about 120° C. In one aspect of Step 6, the reaction temperature is from about 5° C. to about 80° C. In one aspect of Step 6, the reaction temperature is from about 20° C. to about 50° C. In one aspect of Step 6, the reaction temperature is about room temperature (about 25° C.). In one aspect of Step 6, the reaction temperature is about 50° C. The reaction can be conducted in a protic or aprotic solvent or a mixture of two or more solvents. Suitable solvents include, but are not limited to, methanol, ethanol, isopropanol, tert-butanol, and THF. In one aspect of Step 6, the solvent is ethanol. In another aspect of Step 6, the solvent is methanol. In another aspect of Step 6, the solvent is a mixture of methanol and THF. In one aspect of Step 6, ethanol and THF mixture is used as the solvent.

In certain embodiments, compound 7 is produced as a mixture of the 6α-ethyl isomer and the 6β-ethyl isomer. In certain embodiments, the 6β-ethyl isomer is the dominant isomer in the product. In one aspect of Step 6, the crude compound 7 contains less than 20% of 6α-ethyl isomer. In one aspect of Step 6, the crude compound 7 contains less than 10% of 6α-ethyl isomer. In one aspect of Step 6, the crude compound 7 contains less than 5% of 6α-ethyl isomer.

Although compound 7 is shown above as the 6β-ethyl isomer, in embodiments in which the compound is a mixture of the 6-alpha and 6-beta-ethyl isomers, it can be represented as compound 7A below.

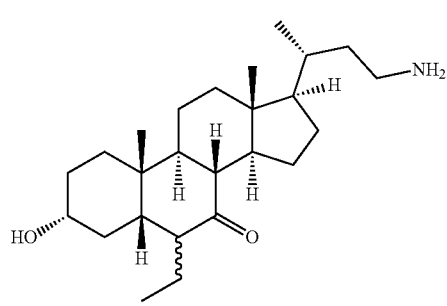

7A

Step 7: converting compound 7 to compound 8:

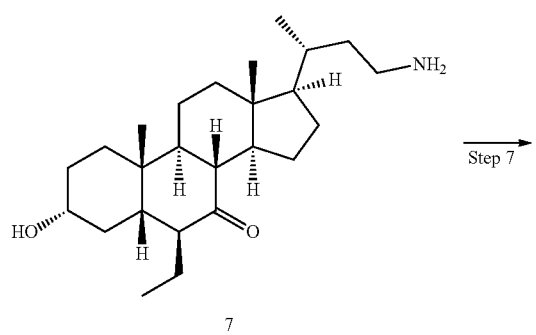

7

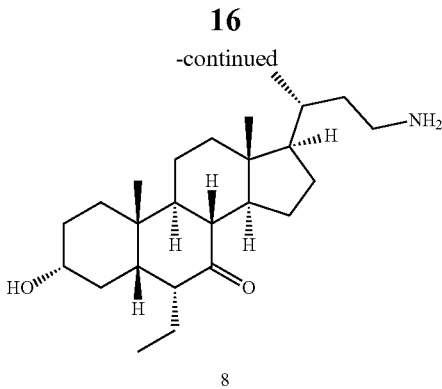

8

Step 7 is the epimerization of the 6β-ethyl isomer of compound 7 to the 6α-ethyl isomer, compound 8, under basic conditions. In one aspect of Step 7, the crude product obtained from Step 6, which contains both 6β-ethyl isomer and 6α-isomer, is used in Step 7 without further purification.

The base can be, but is not limited to, sodium hydroxide or potassium hydroxide. In one aspect, the base is aqueous sodium hydroxide solution. In one aspect of Step 7, the base is a 50% solution of sodium hydroxide in water.

In one aspect of Step 7, the crude product of Step 6 is directly used in Step 7 after removal of the catalyst, such as Pd/C, by filtration. In one aspect of Step 7, the crude product 7 is used after the removal of the catalyst and the solvent.

Step 7 is preferably carried out in a protic solvent such as, but not limited to methanol or ethanol, or a mixture of a protic and non-protic solvent, such as, but not limited to a mixture of methanol or ethanol and THF.

In one aspect of Step 7, the solvent is ethanol. In another aspect of Step 7, the solvent is methanol. In another aspect of Step 7, the solvent is a mixture of ethanol and THF. In another aspect of Step 7, the solvent is a mixture of methanol and THF.

Step 8: converting compound 8 to the compound (II):

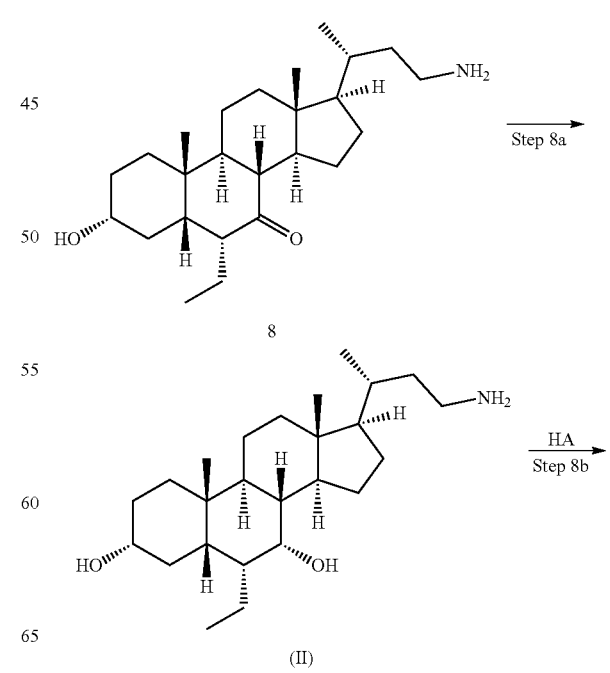

-continued

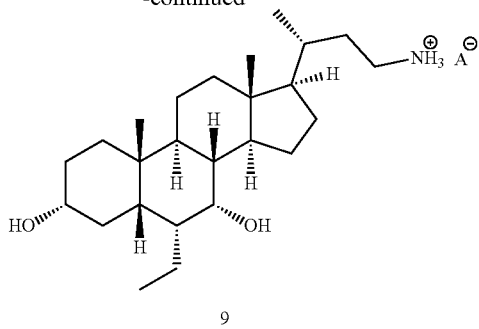

9

Step 8a is the reduction of 7-ketone of compound 8 to form the 7α-hydroxy compound of Formula II. Suitable reducing agents include, but are not limited to, LiBH$_4$, NaBH(OAc)$_3$ and NaBH$_4$. The preferred reducing agent is NaBH$_4$. In one preferred aspect, the crude reaction mixture from Step 7 containing compound 8 is used directly in Step 8a without any work-up, for example, by cooling the mixture to about 0° C. and adding the reducing agent, such as NaBH$_4$. In another aspect, the crude compound 8 is isolated following Step 7, for example, by standard aqueous work-up, and used directly in Step 8 without further purification.

The reaction temperature of Step 8a preferably ranges from about 0° C. to about 100° C. In one aspect of Step 8, the reaction temperature is about 0° C. In one aspect of Step 8a, the reaction temperature is about room temperature (25° C.). In one aspect of Step 8a, the reaction temperature is about 50° C.

Step 8a is carried out in a protic solvent such as, but not limited to, methanol or ethanol or a mixture of protic solvent and an aprotic solvent, such as, but not limited to, a mixture of methanol and THF or ethanol and THF.

Upon the completion of reduction, the reaction mixture is preferably quenched with aqueous NaHCO$_3$ solution and the product is extracted with a mixture of solvents, such as methanol and DCM, ethanol and DCM, or methanol and MTBE.

In Step 8b, the combined extracts containing the compound of Formula II are then acidified with an acid HA to produce compound 9, which is the HA salt of the compound of Formula II. Preferably, HA is a pharmaceutically acceptable acid. Suitable acids HA include, but are not limited to, HCl, TsOH, and H$_2$SO$_4$. Preferably, HA is HCl.

Compound 9 can be crystallized from a solvent system such as, but not limited to, acetonitrile, methanol and DCM, ethanol and DCM, or methanol and MTBE. Preferably, compound 9 is recrystallized from methanol and MTBE.

In one aspect of Step 8a and Step 8b, the purity of compound 9 obtained after the crystallization is greater than 90% by HPLC analysis. In one aspect of Step 8a and Step 8b, the purity of compound 9 obtained after the crystallization is greater than 95% by HPLC analysis. In one aspect of Step 8a and Step 8b, the purity of compound 9 obtained after the crystallization is greater than 98% by HPLC analysis.

From Step 3 to Step 8 according to Scheme 1, compound 4 and compound 9 are preferably purified by crystallization. Compound 5 is preferably used as the crude product without purification. Compound 6, compound 7 and compound 8 are preferably obtained either as crude materials and used directly in the next step or, more preferably, used directly without isolation in a one-pot manner. Compound 7 and compound 8 can also be separated as their HA salts.

Process to Prepare a Compound of Formula (I)

The current invention also includes a process for preparing a compound of formula (I) starting with the compound (II) as shown in Scheme 2.

Scheme 2

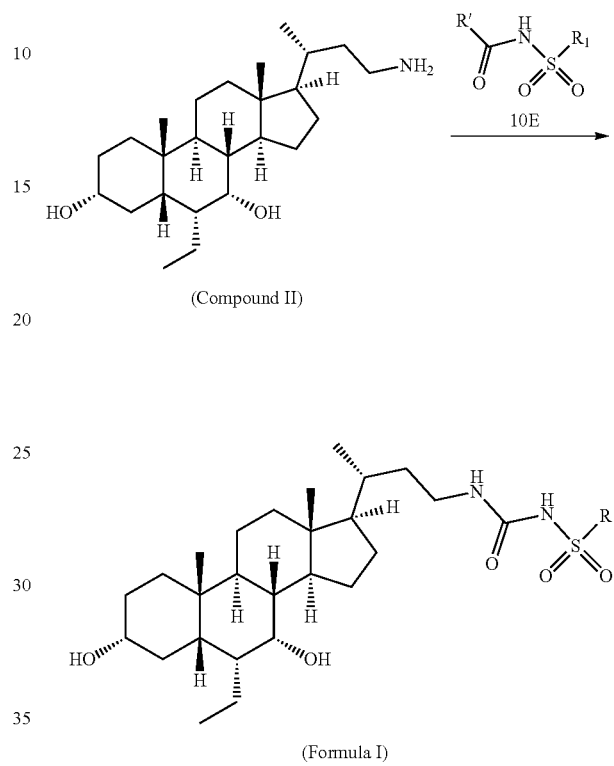

The process involves converting the compound (II) to the compound of Formula (I), wherein R$_1$ is as previously defined, by reacting the compound (II) with a compound represented by 10E wherein, R' is imidazol-1-yl, alkyl-O—aryl-O, C$_1$, or CCl$_3$, in the presence of an organic base. The reaction is preferably carried out in an aprotic solvent, such as, but not limited to, THF, DCM or toluene. In another aspect, the reaction solvent is a mixture of an aprotic solvent, such as THF, DCM or toluene, with a protic solvent, such as isopropanol, EtOH or MeOH. In one preferred aspect, the reaction solvent is a mixture of toluene and isopropanol. Suitable organic bases include, but are not limited to, trimethylamine and diisopropylethylamine. The reaction temperature preferably ranges from about 0° C. to about 80° C. In one aspect, the reaction is carried out at about 0° C. In another aspect, the reaction is carried out at about room temperature (about 25° C.). In yet another aspect, the reaction is carried out at about 50° C.

Preferably R' in compound 10E is imidazol-1-yl, MeO—, EtO- or PhO—. More preferably, R' is PhO—.

The solvent, organic base and reaction conditions used in this reaction can also be used in the preparation of the compound (III) shown in Scheme 3.

Process to Prepare Compound (III)

The process of the current invention also includes a process of preparation of compound (III) starting of compound (II) following the process described in Scheme 3.

Scheme 3

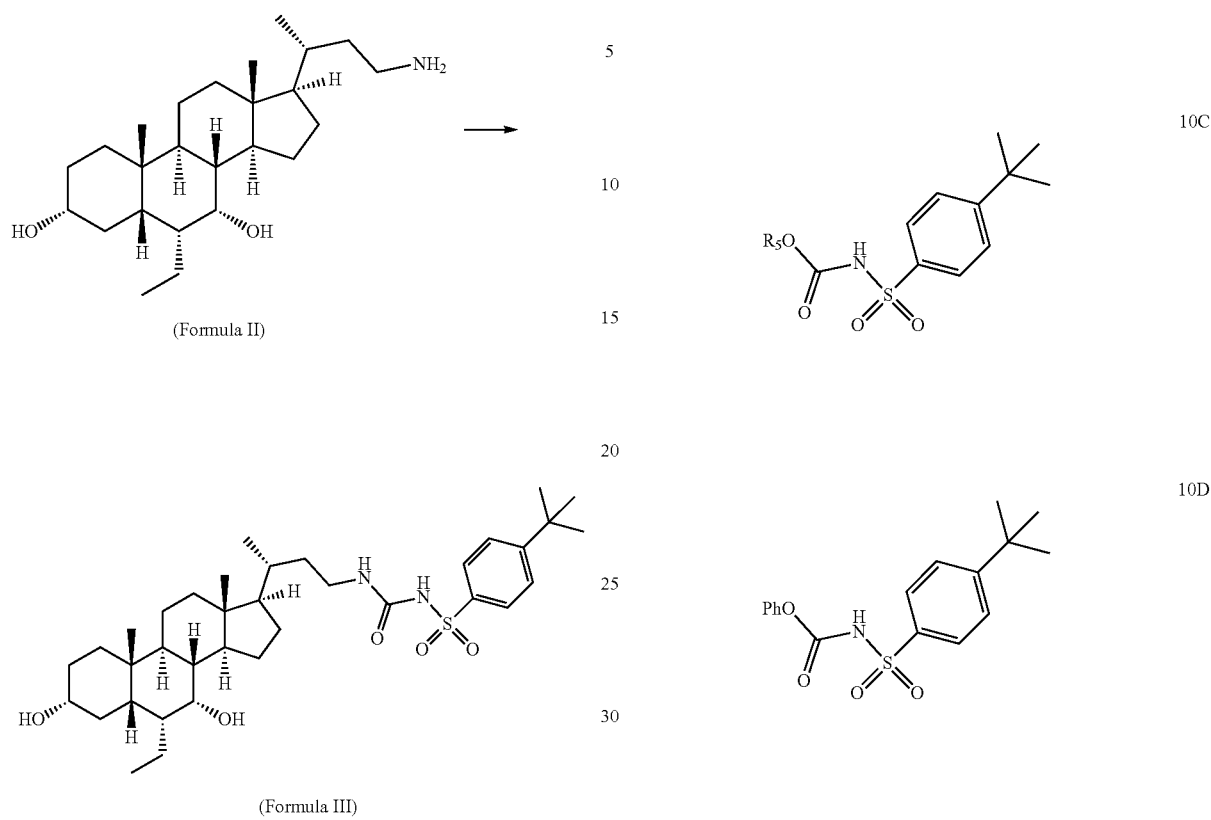

The process involves the conversion of amine compound (II) to sulfonyl urea compound (III) with an appropriate reagent, such as those shown below, in the presence of organic base.

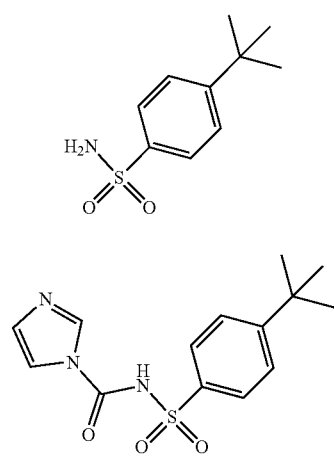

In one aspect, the reagent is 10B which can be formed by reacting sulfonamide compound 10A with CDI.

In another aspect, the said reagent can be sulfonylcarbamate compound 10C, wherein $R_5$ is alkyl or aryl, preferably methyl, ethyl, or phenyl. The preferred reagent is 10D.

In one aspect, the amine compound (II) reacts with 10D in an aprotic solvent, such as, but not limited to, THF, DCM or toluene. In another aspect, the reaction solvent is a mixture of an aprotic solvent, such as THF, DCM or toluene, with a protic solvent, such as isopropanol, EtOH or MeOH. In one preferred aspect, the reaction solvent is a mixture of toluene and isopropanol. Suitable organic bases include, but are not limited to, triethylamine and diisopropylethylamine. The reaction temperature preferably ranges from about 0° C. to about 80° C. In one aspect, the reaction is carried out at about 0° C. In another aspect, the reaction is carried out at about room temperature (about 25° C.). In yet another aspect, the reaction is carried out at about 50° C.

Preferably, the amount of sulfonyl reagent 10B or 10C, for example compound 10D, used in this process is chosen to minimize the formation of byproduct 11, with structure shown below. The presence of the excess amount of compound 10D in the reaction mixture, for example, tends to result in formation of the byproduct 11. In the reaction solvent system which contains protic solvent, such as isopropanol, the formation of byproduct 11 can be minimized.

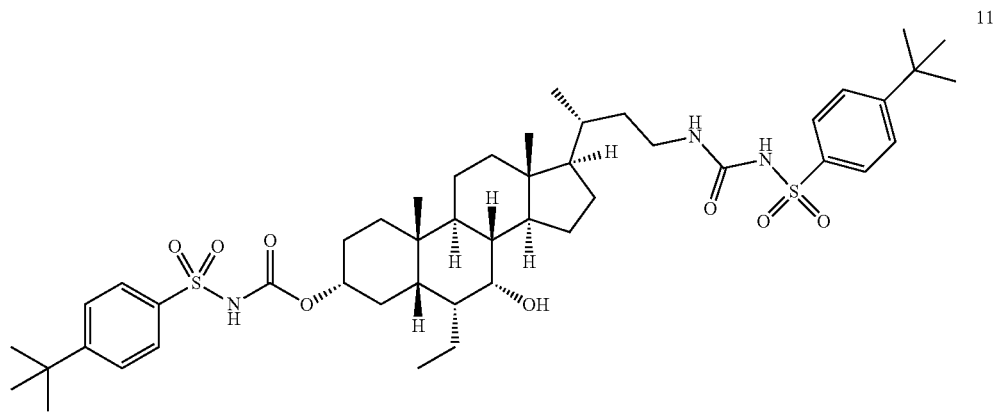

In one aspect, the molar ratio of the compound (II) and compound 10D is about 1 to 1. In another aspect, the molar ratio of the compound (II) and compound 10D is about 1 to 1.05. In yet another aspect, the molar ratio of the compound of formula II and compound 10D is about 1 to 1.1. In yet another aspect, the molar ratio of the compound (II) and compound 10D is 1 to 1.15.

Process for Preparing a Crystalline Form of Compound of Formula (I) Diethylammonium Salt In another embodiment, the present invention provides a process for preparing a crystalline form of a diethylammonium salt of a compound of Formula (I), as shown in Scheme 4.

Scheme 4

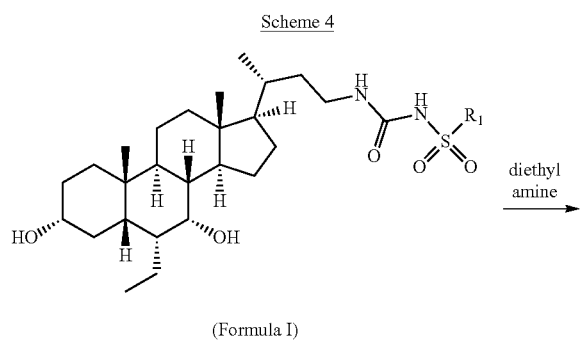

-continued (Formula IV)

The process comprises treating the compound of Formula (I) with an excess of diethylamine in solution, thereby forming the diethylammonium salt of the compound of Formula (I), shown in Scheme 4 as Formula (IV). In one embodiment, the compound of Formula (I) is reacted with diethylamine as the crude product of the process shown in Scheme 2. That is, the compound of Formula (I) can be reacted with diethylamine without isolating and/or purifying the compound. In another embodiment, the compound of Formula (I) is isolated and/or purified prior to the reaction with diethylamine.

Process to Prepare Crystalline Form of Compound (III) Diethylammonium Salt

In another embodiment, the present invention provides a process preparing a crystalline form of the diethylammonium salt of the compound (III), as shown in Scheme 5.

Scheme 5

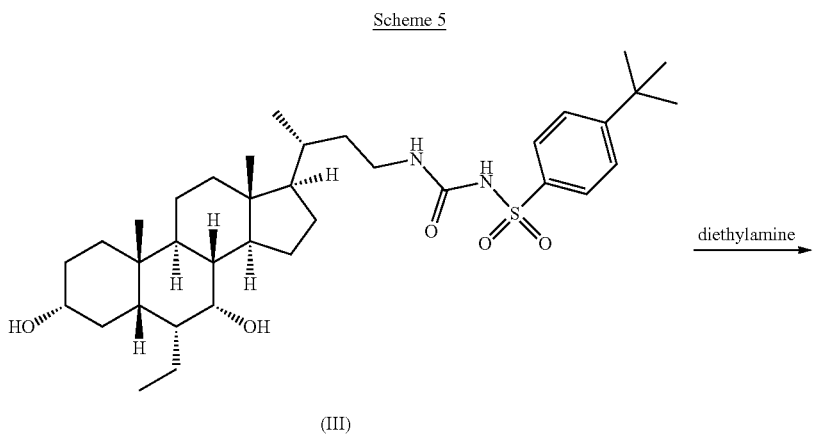

(III)

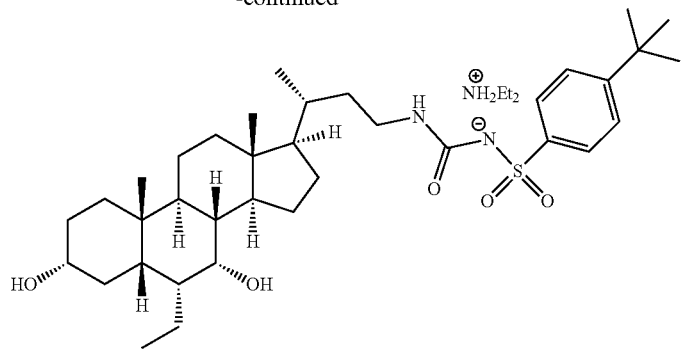

12

Scheme 5 describes the formation of the product 12, the diethylammonium salt of the compound (III), which is preferably crystalline and of high purity. In one aspect, the crude compound (III) following the process of Scheme 3 is used after acidic work-up without any further purification. In another embodiment, the compound (III) is isolated and/or purified prior to the reaction with diethylamine. Suitable solvents for use in this process include, but are not limited to, acetone, isopropyl acetate, and ethyl acetate. Preferably the solvent is acetone. Upon treatment of the crude compound (III) with diethylamine in acetone, compound 12 slowly crystallizes from solution as a crystalline material. The molar ratio of diethyl amine to compound (III) in the salt formation process preferably ranges from about 1:1 to about 10:1.

In one aspect, the molar ratio of diethyl amine to compound (III) ranges from about 1:1 to about 5:1. In another aspect, the molar ratio of diethyl amine to compound (III) ranges from about 1.2:1 to about 3:1. In yet another aspect, the molar ratio of diethyl amine to compound (III) ranges from about 1.2:1 to about 2:1.

In one embodiment, after reaction, compound 12 is crystallized from the crude reaction mixture directly. In one aspect, compound 12 is obtained with greater than about 90% purity after crystallization. In another aspect, compound 12 is obtained with greater than about 95% purity after crystallization. In yet another aspect, compound 12 is obtained with greater than about 98% purity after crystallization.

In another embodiment, compound 12 is recrystallized from a solvent, such as, but not limited to, acetone, isopropyl acetate, or ethyl acetate.

In another embodiment, compound 12 is recrystallized from a mixture of solvents, such as, but not limited to, MeOH and acetone, ethyl acetate and acetone, or toluene and acetone. In one aspect, the MeOH is added first to dissolve compound 12, then concentrate the solution by partially removing MeOH, followed by adding acetone to generate crystal form of compound 12. In one aspect, the compound 12 is dissolved in a mixture of methanol and acetone, preferably in a range from 5% to 20% methanol by volume, by heating to about 40-50° C. The solution is then cooled to 0° C. to room temperature to generate a crystalline form of compound 12. Preferably, the volume ratio of methanol to acetone is 1:9. In one aspect, compound 12 is obtained with greater than about 90% purity after recrystallization. In another aspect, compound 12 is obtained with greater than about 95% purity after recrystallization. In yet another aspect, compound 12 is obtained with greater than about 98% purity after recrystallization.

Process for Preparing an Amorphous Form of the Compound of Formula (I)

In another embodiment, the present invention provides a process for preparing amorphous solid form of the compound of formula (I), starting from the diethylammonium salt of formula (IV). This process is shown in Scheme 6.

Scheme 6

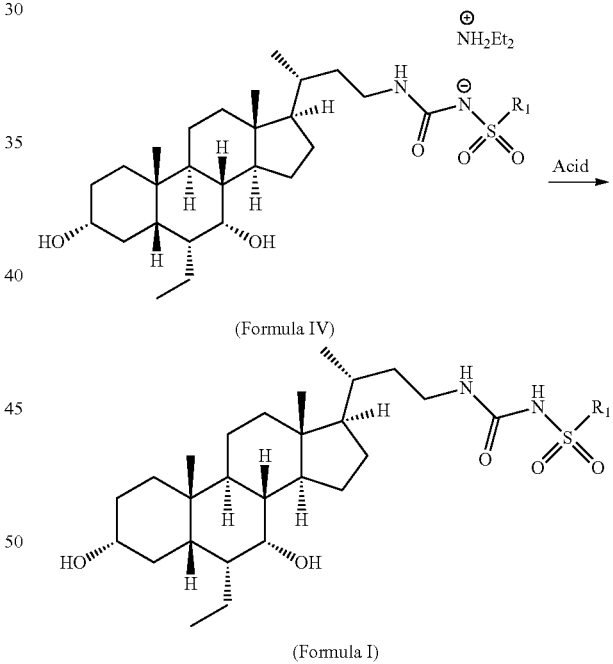

(Formula IV)

(Formula I)

The process comprises the step of treating the compound of Formula (IV) with an acid in solution to form the compound of Formula (I), and then isolating the amorphous solid form of the compound of Formula (I). In one aspect, the acid used is citric acid. In another aspect, the acid used is HCl.

Process for Preparing an Amorphous Form of Compound (III)

In another embodiment, the present invention provides a process for preparing an amorphous solid form of the compound (III) starting with compound 12. The process is illustrated in Scheme 7.

Scheme 7

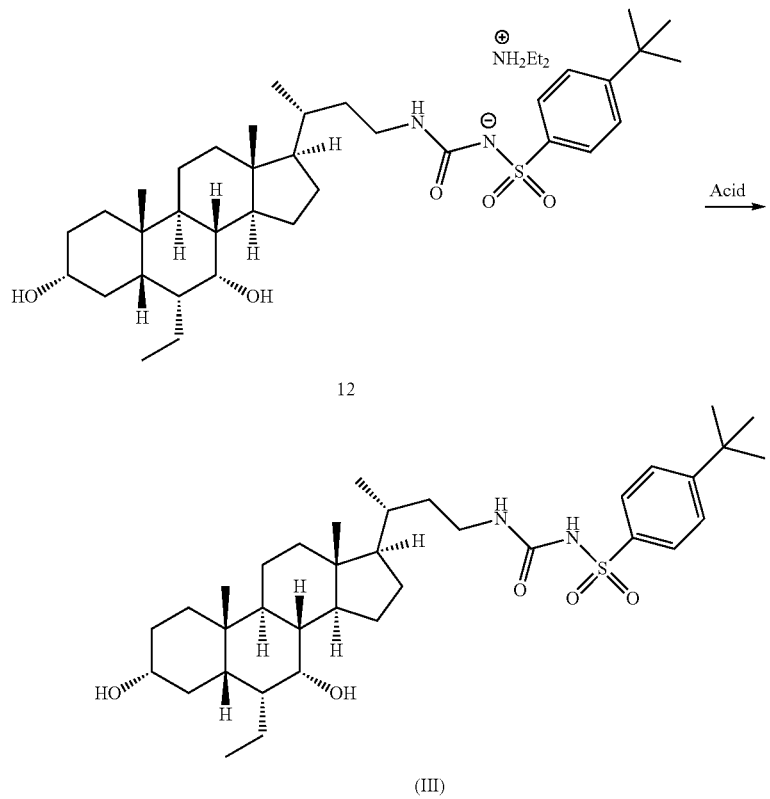

The method comprises reacting compound 12 with an acid in solution to produce the compound (III) and isolating an amorphous form of the compound (III). In one aspect, the acid used is citric acid. In another aspect, the acid is HCl. In one embodiments, compound 12 is reacted with the acid by washing a solution of compound 12 in an organic solvent such as, but not limited to, EtOAc, DCM, or iPrOAc, with an aqueous solution of the acid. In one aspect, the organic solvent is EtOAc. In one aspect, the aqueous acid solution is 10% citric acid in water. Preferably, the process further comprises drying and concentrating the organic phase provide the amorphous solid form of the compound of formula III. In another embodiment, the solution of compound 12 is washed with acid and then solvent exchange to methanol. The methanol solution is added to water to form a precipitate, which is preferably isolated by filtration to provide an amorphous solid form of compound III.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl radicals include $C_1$-$C_6$ alkyl and $C_1$-$C_8$ alkyl radicals. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, cyclooctyl, bicyclo[2.2.1]heptyl, bicyclo[2.2.2]octyl, spiro[2.5]octyl, 3-methylenebicyclo[3.2.1]octyl, spiro[4.4]nonanyl, bicycle[3.1.0]hexanyl, spiro[2.3]hexanyl, bicycle[3.1.1]

heptanyl, spiro[2.5]octanyl, bicycle[4.1.0]heptanyl, bicycle[3.1.0]hexan-6-yl, spiro[2.3]hexan-5-yl, bicycle[3.1.1]heptan-3-yl, spiro[2.5]octan-4-yl, and bicycle[4.1.0]heptan-3-yl and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The terms "heterocyclic" or "heterocycloalkyl" can be used interchangeably and referred to a non-aromatic ring or a bi- or tri-cyclic group fused, bridged or spiro system, wherein (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "arylalkyl," as used herein, refers to a functional group wherein an alkylene chain is attached to an aryl group, e.g., —CH$_2$CH$_2$-phenyl. The term "substituted arylalkyl" means an arylalkyl functional group in which the aryl group is substituted. Examples include, but are not limited to, benzyl, phenethyl and the like. Preferred arylalkyl groups include aryl-$C_1$-$C_8$-alkyl groups.

The term "heteroaryl," as used herein, refers to a mono-, bi-, or tri-cyclic group comprising at least one 5- or 6-membered aromatic ring comprising at least one ring atom selected from S, O and N. Preferred heteroaryl groups are monocyclic or bicyclic. Heteroaryl groups include monocyclic groups having 5 or 6 ring atoms and fused bicyclic groups comprising 8 to 10 ring atoms. Heteroaryl groups include, but are not limited to, pyridinyl, pyrazolyl, pyrazinyl, pyrimidinyl, pyrrolyl, pyrazolyl, imidazolyl, thiazolyl, thienyl, triazolyl, isothiazolyl, oxazolyl, isoxazolyl, thiadiazolyl, oxadiazolyl, thiophenyl, furanyl, quinolinyl, isoquinolinyl, benzimidazolyl, benzooxazolyl, benzothienyl, quinoxalyl, indolyl, indazolyl, benzisoxazolyl, benzofuranyl, benzotriazolyl, benzothiazolyl, and the like.

The term "heteroarylalkyl," as used herein, refers to an alkylene chain is attached to a heteroaryl group. The term "substituted heteroarylalkyl" means a heteroarylalkyl functional group in which the heteroaryl group is substituted. Examples include, but are not limited to, pyridinylmethyl, pyrimidinylethyl and the like. Preferred heteroarylalkyl groups include heteroaryl-$C_1$-$C_8$-alkyl groups.

The term "biaryl", as used herein, refers to a moiety consisting of two aryl groups, two heteroaryl groups or an aryl group and a heteroaryl group, wherein the two groups are connected by a single bond. A substituted biaryl group is a biaryl moety in which at least one of the connected groups has at least one non-hydrogen substituent. Examples of biaryl groups include biphenyl, pyridylphenyl, pyrimidylphenyl, pyrimidypyridyl, and pyrimidyloxadizolyl groups.

The term 'aryl-heterocyclyl' refers to a bicyclic group comprising a monocyclic aryl or heteroaryl group connected to a heterocyclic group by a single bond. Examples of aryl-heterocyclyl groups include phenyl-piperidinyl and pyridyl-piperidinyl groups.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —NO$_2$, —N$_3$, —CN, —NH$_2$, protected amino, oxo, thioxo, —NH—$C_1$-$C_{12}$-alkyl, —NH—$C_2$-$C_5$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)— heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —CO$_2$—$C_2$-$C_8$ alkenyl, —CO$_2$—$C_2$-$C_8$ alkynyl, CO$_2$—$C_3$-$C_{12}$-cycloalkyl, —CO$_2$-aryl, CO$_2$-heteroaryl, CO$_2$-heterocyloalkyl, —OCONH$_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_8$-alkenyl, —NHCO$_2$— $C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —SO$_2$NH$_2$, —SO$_2$NH—$C_1$-$C_{12}$-alkyl, —SO$_2$NH—$C_2$-$C_8$-alkenyl, —SO$_2$NH—$C_2$-$C_8$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_8$-alkenyl, —NHSO$_2$—$C_2$-$C_8$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S— heterocycloalkyl, or methylthiomethyl. It is understood that the aryls, heteroaryls, alkyls, cycloalkyls and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2*, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic α, β, γ, or δ amino acids, and includes but is not limited to, amino acids found in proteins or intermediates in metabolism of amino acids or proteins, i.e., glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is $-NR^u\text{-}G(S_c)-C(O)\text{-}Q^1$, wherein $Q^1$ is $-SR^v$, $-NR^vR^v$ or alkoxyl, $R^v$ is hydrogen or alkyl, $S_c$ is a side-chain of a naturally occurring or non-naturally occurring amino acid, G is $C_1\text{-}C_2$ alkyl, and $R^u$ is hydrogen; or $R^u$ and $S_c$ are taken together with the atoms to which they are attached to form a five-membered heterocyclic ring. In an embodiment, an amino acid derivative is provided as a substituent of a compound described herein, wherein the substituent is $-O-C(O)\text{-}G(S_c)-NH\text{-}Q^2$, wherein $Q^2$ is hydrogen or alkoxyl, $S_c$ is a side-chain of a naturally occurring or non-naturally occurring amino acid and G is $C_1\text{-}C_2$ alkyl. In certain embodiments, $Q^2$ and $S_c$ are taken together with the atoms to which they are attached to form a five-membered heterocyclic ring. In certain embodiments, G is an optionally substituted methylene and $S_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

When the compounds described herein contain one or more asymmetric centers they give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus, a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof.

Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e., causing regression of the disease state or condition. Treating can also include inhibiting, i.e., arresting the development, of an existing disease state or condition, and relieving or ameliorating, i.e., causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Abbreviations

Abbreviations which have been used in the descriptions of the schemes and the examples that follow are:
Ac for acetyl;
AcOH for acetic acid;
ACN for acetonitrile;
AIBN for azobisisobutyronitrile;
aq. for aqueous;
$Boc_2O$ for di-tert-butyl-dicarbonate;
Boc for t-butoxycarbonyl;
BPO for benzoyl peroxide;
Bz for benzoyl;
Bn for benzyl;
t-BuOK for potassium tert-butoxide;
$Bu_3SnH$ for tributyltin hydride;
Brine for sodium chloride solution in water;
n-BuLi for n-butyl lithium;
i-BuLi for i-butyl lithium;
t-BuLi for t-butyl lithium;
t-BuOH for tert-butanol;
$Bu_4NBr$ for tetrabutylammonium bromide;
$Bu_4NCl$ for tetrabutylammonium chloride;
$Bu_4NI$ for tetrabutylammonium iodide;
Cbz for carbobenzyloxy;
CDI for carbonyldiimidazole;
DBU for 1,8-diazabicyclo[5.4.0]undec-7-ene;
DCC for N,N'-dicyclohexylcarbodiimide;
DCE for 1,2-dichloroethane;
DIBAL-H for diisobutylaluminium hydride;
DIPEA or $(i-Pr)_2EtN$ for N,N-diisopropylethyl amine;
Dess-Martin periodinane for 1,1,1-tris(acetyloxy)-1,1-dihydro-1,2-benziodoxol-3-(1H)-one;
DMAP for 4-dimethylamino-pyridine;
DME for 1,2-dimethoxyethane;
DMF for N,N-dimethylformamide;
DMSO for dimethyl sulfoxide;
DPPA for diphenyl phosphoryl azide;
EDC for N-(3-dimethylaminopropyl)-N'-ethylcarbodiimide;
EDC·HCl for N-(3-dimethylamino-propyl)-N'-ethylcarbodiimide hydrochloride;
EtOAc for ethyl acetate;
EtOH for ethanol;
$Et_2O$ for diethyl ether;
eq. for equivalent;
Fmoc for 9-fluorenylmethoxycarbonyl;
HATU for O-(7-azabenzotriazol-1-yl)-N,N,N',N'-tetramethyluronium hexafluorophosphate;
hrs for hours;
KHMDS for potassium bis(trimethylsilyl)amide;
Ph for phenyl;
PhLi for phenyl lithium;
LDA for lithium diisopropylamide;
LiHMDS for lithium bis(trimethylsilyl)amide;
MOM for methoxymethyl;
MEM for 2-methoxyethoxymethyl;
MTBE for methyl t-butyl ether;
Ms for mesyl;
min for minutes;
NaHMDS for sodium bis(trimethylsilyl)amide;
NMO for N-methylmorpholine N-oxide;
o/n for overnight;
PDC for pyridinium dichromate;
i-PrOAc for isopropyl acetate;
Ph for phenyl;
PMB for p-methoxybenzyl;
RT or rt for room temperature;
sat. for saturated;
SEM for (trimethylsilyl)ethoxymethyl;
TBAF for tetrabutylammonium fluoride;
TBS for tert-butyl dimethylsilyl;
TEA or $Et_3N$ for triethylamine;
TFA or $CF_3COOH$ for trifluoroacetic acid;
THF for tetrahydrofuran;
TMEDA for N,N,N',N'-tetramethylethylenediamine;

TPP or PPh₃ for triphenylphosphine;
Ts for tosyl or —SO₂—C₆H₄CH₃;
TsOH for p-tolylsulfonic acid;
TMS for trimethylsilyl;
TMSCl for trimethylsilyl chloride;
TMSOTf for trimethylsilyl trifluoromethanesulfonate;
TBS for tert-butyl(dimethyl)silyl;
TBSCl for tert-butyl(dimethyl)silyl chloride;
TES for triethylsilyl;
TBDPS for tert-butyl(diphenyl)silyl;
TIPS for triisopropylsilyl;
THP for tetrahydropyranyl;
TTMSS or (Me₃Si)₃SiH for tris(trimethylsilyl)silane
TBME for tert-butyl methyl ether;
Tf₂O for trifluoromethanesulfonic anhydride;
TLC for thin layer chromatography;
(TMS)₂NH for hexamethyldisilazane;
TMSOTf for trimethylsilyl trifluoromethanesulfonate;
TPAP tetrapropylammonium perruthenate;
TPP or PPh₃ for triphenylphosphine;
TrCl for trityl chloride.

All other abbreviations used herein, which are not specifically delineated above, shall be accorded the meaning which one of ordinary skill in the art would attach.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the Scope of the Appended Claims.

Example 1. Preparation of Compound 2-E from Compound 1

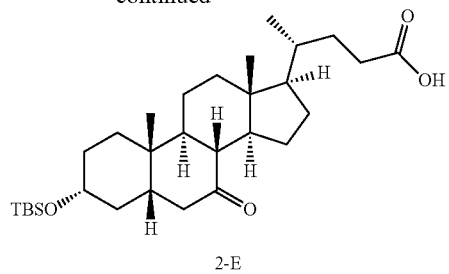

2-E

To a solution of compound 1 (2.5 kg, 6.4 mol, 1.0 eq) in anhydrous THF (20.0 L, 8 v) and anhydrous DMF (5.0 L, 2 v) in a 50 L flask under N₂ at 5° C. was charged imidazole (2.6 kg, 38.4 mol, 6.0 eq) in portions to maintain the internal temperature below 5° C. A solution of TBSCl (2.10 kg, 14.1 mol, 2.2 eq) in anhydrous toluene (2.5 L, 1 v) was added slowly to maintain the internal temperature below 10° C. The reaction mixture was stirred at 15±5° C. for ~2 hrs and monitored by HPLC until compound 1 was ≤0.5%.

Methanol (5.0 L, 2.0 v) and K₂CO₃ (442.0 g, 3.2 mol, 0.5 eq) were added and the reaction mixture was stirred for ~2 hrs at 20±5° C. until HPLC indicated that 3,24-bis-TBS intermediate was converted to compound 2-E completely.

The reaction mixture was then cooled to 5° C. and adjusted to pH ~7 by charging aq. HCl (2N, 9.3 L, 3.7 v) slowly to maintain the internal temperature below 15° C. The pH was further adjusted to 4-5 by charging 10 wt % aq. citric acid (12.5 L, 2.5 v). The mixture was extracted once with toluene (25 L, 10 v). The organic layer was separated, washed with water (2×10 kg, 2×4 v) and concentrated to ~3 v. 4 v heptane was added and the mixture was concentrated to ~3 v. Additional 4 v heptane was added and the mixture was concentrated to ~5v. The resulting solution which contained lots of white solid suspension was allowed to cool to 15±5° C. and filtered. The filter cake was washed with heptane (2.5 L, 1v) and dried under high vacuum at 40±5° C. for 16 hrs to provide the desired compound 2-E (2.9 kg, 89.8% yield, HPLC, ELSD purity: 99.0%) as a white solid.

Example 2. Preparation of Compound 3-E from Compound 2-E

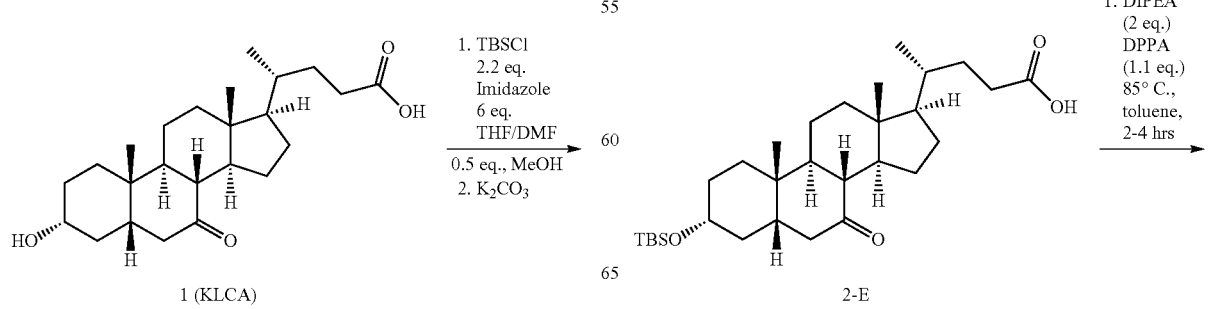

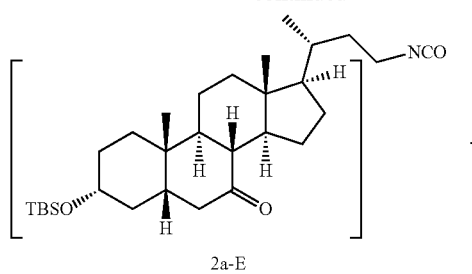

2a-E

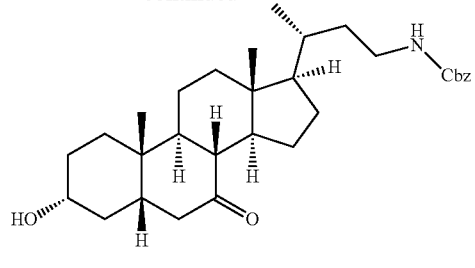

4-E

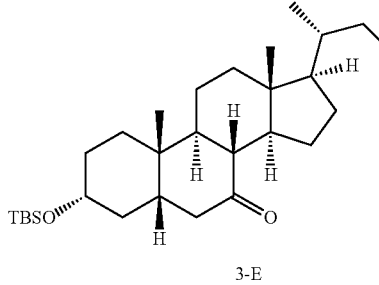

3-E

Compound 2-E (103 g, ~204 mmol) was dissolved in anhydrous toluene (800 mL, 8v) in a flask to which a sweep of nitrogen gas was applied continuously during the entire reaction process. DIPEA (71.3 mL, 409 mmol, 2 eq) was added and the resulting mixture was heated to ~85° C. A solution of DPPA (62 g, 225 mmol, 1.1 eq) in anhydrous toluene (160 mL, 2v) was added dropwise slowly to maintain the internal temperature to ~85±5° C. during the addition. After the completion of addition of DPPA in about 2-3 hrs, the reaction mixture was heated at ~85° C. for additional 2~3 hrs. BnOH (24.35 g, 225 mmol, 1.1 eq) was then added followed by DBU (62.3 g, 409 mmol, 2 eq).

The resulting cloudy mixture was stirred at rt overnight and then quenched by slow addition of 10% aq. citric acid (800 mL, 10v) at <25° C. The mixture was extracted once with toluene (400 mL, 5v) and separated. The organic layer was washed with aq. 10% citric acid (800 mL, 10v), H$_2$O (2×10v), aq. sat. NaHCO$_3$ (800 mL, 10v), dried with Na$_2$SO$_4$, concentrated and further dried under high vacuum to afford the crude compound 3-E (124.5 g, contained ~4% of BnOH), which was used directly in the next step. LC-MS, ES$^+$(m/z): 627.50 (M+NH$_4^+$).

Example 3. Preparation of Compound 4-E from Compound 3-E

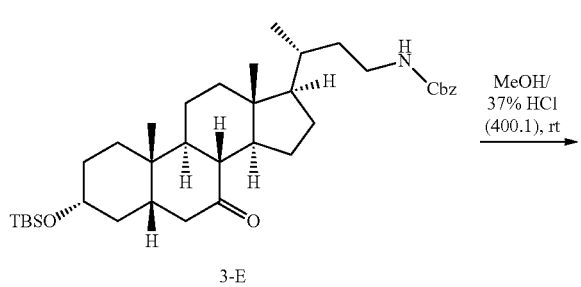

3-E

To a solution of the crude compound 3-E from the last step (~112 g, ~183 mmol) in MeOH (500 ml, 4.4v) at rt was added 37% HCl in water (1.26 mL). The solid product started to precipitate out after ~30 min. After stirring at rt overnight, the resulting solid precipitation was collected by filtration, rinsed with chilled MeOH (~50 to 100 mL, 0.5 v to 1v) and dried under high vacuum overnight at 30° C. to afford a white crystalline solid compound 4-E (56.8 g, 62.4% overall yield for 4 steps from KCLA, HPLC purity=99.4% @UV 210 nm). LC-MS, ES$^+$(m/z): 513.37 (M+NH$_4^+$).

Example 4. Preparation of Compound 5-E from Compound 4-E

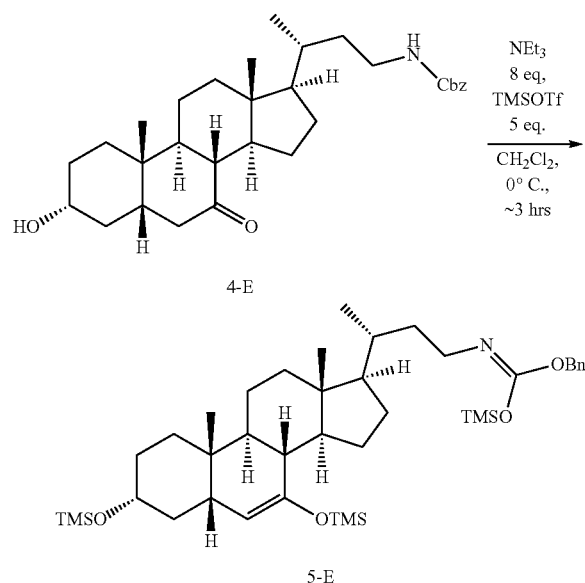

4-E

5-E

To a solution of compound 4-E (45 g, 91 mmol) and triethylamine (101 mL, 726 mmol, 8 eq) in anhydrous CH$_2$Cl$_2$ (900 mL, 20v) at 0° C. under N$_2$ was added TMSOTf (82 mL, 454 mmol, 5 eq) dropwise over 30 min to maintain the internal temperature under 5° C. After stirring at 0° C. for ~2 hrs, TLC showed a complete consumption of sm. The reaction solution was then added to a solution of sat. NaHCO$_3$ solution (400 mL, ~9 v) at 0° C. slowly over 3 hrs to maintain the internal temperature at <10° C. The resulting organic layer was separated and washed with water (3×1 L), brine (500 mL), dried, and concentrated. The residue oil was re-dissolved in hexanes (1 L) and washed with water (1 L), sat NaHCO$_3$ (800 mL), water (800 mL), brine (500 mL), dried over Na$_2$SO$_4$, concentrated and further dried under high vacuum to give compound 5-E (62.7 g) as a white solid, which was used directly in the next step.

Example 5. Preparation of Compound 6-E from Compound 5-E

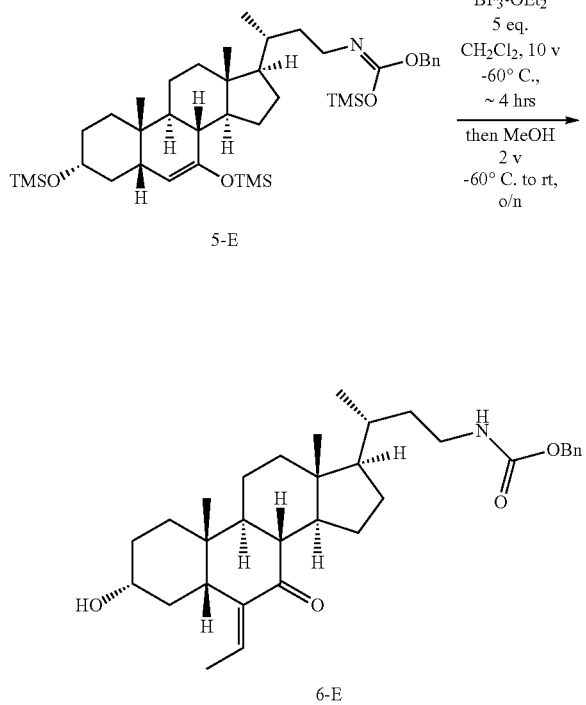

To a solution of compound 5-E (61 g, ~81 mmol) in anhydrous DCM (570 mL, ~9v) at −60° C. (internal temperature) under N$_2$ was added cold CH$_3$CHO (12.09 mL, 214 mmol, 2.5 eq) followed by dropwise addition of BF$_3$.Et$_2$O (54.3 mL, 428 mmol, 5 eq) slowly to maintain the internal temperature below −60° C.

After stirring at −60° C. for 2-3 hrs (LC-MS and HPLC indicated that the initial Aldol HO intermediates were formed as the major products), MeOH (120 mL, 2 v) was added dropwise over 20 min to quench the reaction. The resulting mixture was allowed to warm up to 10° C. to 15° C. slowly. After stirring overnight, the reaction was quenched by adding the mixture to a precooled solution of sat. NaHCO$_3$ (1 L) at 0° C. The organic layer was separated and washed with H$_2$O (300 mL), brine (300 mL), dried (Na$_2$SO$_4$) and concentrated to provide the crude product 6-E as an off-white solid (47.4 g). LC-MS, ES$^+$(m/z): 539.46 (M+NH$_4^+$). The crude compound 6-E was used directly in the next step.

Example 6: Preparation of Compound 9-E from Compound 6-E

Method A

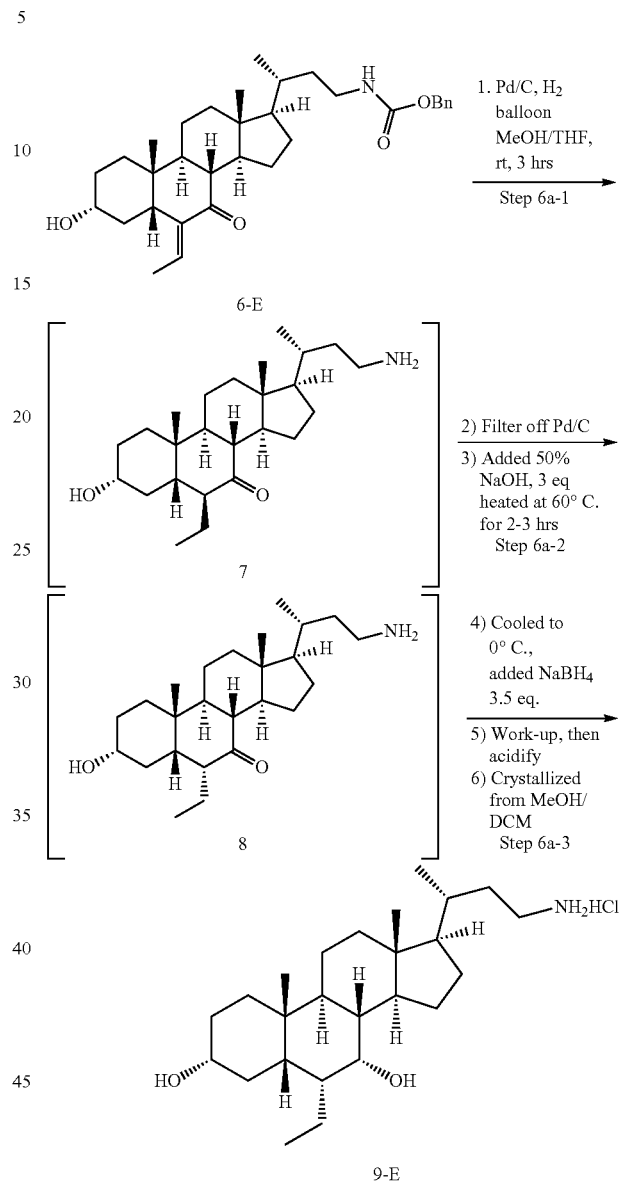

To a mixture of compound 6-E (10 g, ~19.1 mmol, the crude product from the previous step) in THF (30 mL, 3v) and EtOH (30 mL, 3v) at room temperature (about 25° C.) was added Pd/C (contained 50% water, 10% Pd on dry basis, 1.02 g, 0.48 mmol, 0.025 eq.). The reaction mixture was stirred at rt under a H$_2$ balloon for 3 hrs and monitored by LC-MS and HPLC. Upon completion, the catalyst was filtered through celite and rinsed with EtOH (2×10 mL) and the filtrate containing compound 7 was used directly in the next step. LC-MS, ES$^+$(m/z): 390.34 (M+1).

To a 250 mL round bottom flask containing compound 7 (~19.1 mmol) in THF (30 mL)/EtOH (50 mL) at rt was added 50% NaOH in water (3.04 mL, 57.5 mmol, 3 eq.). The reaction mixture was heated at 60° C. under N$_2$ and monitored by LC-MS and HPLC. After 2-3 hrs, HPLC and LC-MS indicated the complete formation of compound 8. LC-MS, ES$^+$(m/z): 390.34 (M+1).

The reaction mixture containing compound 8 (~19.1 mmol) was cooled down to 0° C. with an ice-water bath. NaBH$_4$ (2.54 g, 67.1 mmol, 3.5 eq) was added portion wise. The reaction mixture was allowed to warm up to rt slowly and stirred overnight and monitored by HPLC and LC-MS. If there was still compound 8 left, heated the reaction to 35° C. for several hours to push the reaction to completion. Additional NaBH$_4$ (up to 1 eq) can be added as well, if needed. After the complete consumption of compound 8, the reaction was cooled to 0° C. and quenched by dropwise addition of aqueous sat. NaHCO$_3$ solution (~200 mL). The resulting mixture was extracted with DCM (200 mL) once and one more time with 20% MeOH in DCM (240 mL). To the combined organic layers at rt was added 2N HCl in ether (30 mL, 60 mmol, ~3 eq) dropwise with stirring. The resulting mixture was concentrated slowly under reduced pressure at 35° C. (water bath temperature) to remove ~200 mL of solvents. Lots of colorless solid formed during concentration. The resulting mixture was diluted with DCM (200 mL) and concentrated again to remove ~200 mL of solvents. Another ~50 mL of DCM was added to the remaining mixture which contained lots of colorless solid product at 35° C. and the mixture was allowed to cool to rt slowly overnight to complete the crystallization process. The solid product was collected by filtration, rinsed with DCM (3×), and dried to provide compound 9-E HCl salt as a colorless solid (6.8 g, 83% yield in 5 steps from compound 4-E). Compound 9-E: LC-MS, ES$^+$(m/z): 392.35 (M+1).

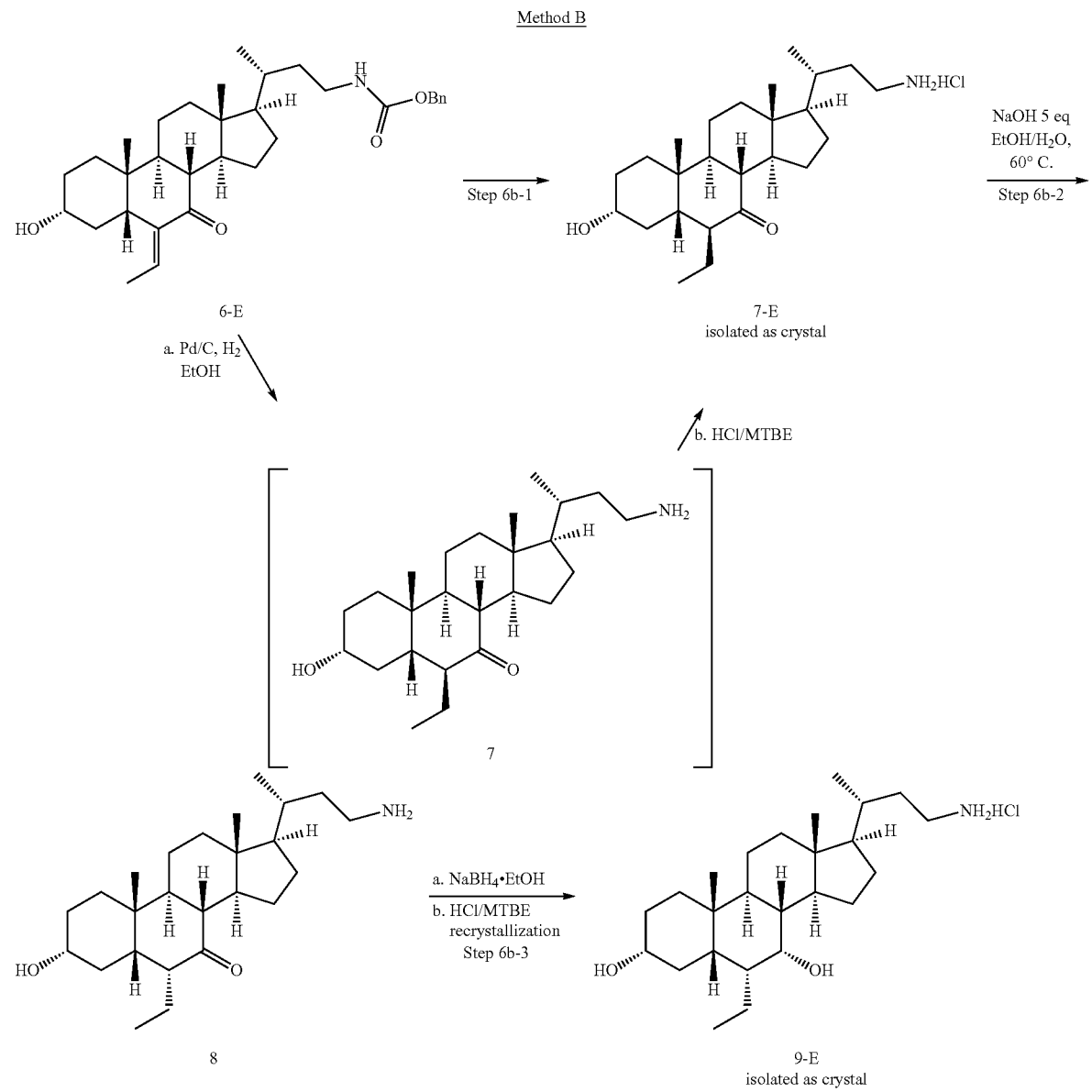

Step 6b-1, charged the solution of compound 6-E in EtOH (10 v), wet 10% Pd/C (50% water, 25% wt) to a hydrogenation reactor, 10 wt % Pd/C was used in small scale. Reactor was vacuumed and then inerted with nitrogen atmosphere, then applied hydrogen pressure to 2-3 atms. Repeat the procedure of applying hydrogen pressure to 2-3 atms for 3 times. The solution was stirred at 25±5° C. and 2-3 atms hydrogen atmosphere for about 12 hours.

Monitored the reaction by HPLC (and LC-MS) until the content of compound 6-E≤0.5% & compound 7≤0.5%. Compound 7-E and compound 7 is not separating in normal HPLC method. Filtered and collected the filtrate, washed the filter cake with 2 v EtOH, concentrated the organic solution to 2.0 v, charged MTBE (4v) & 2N HCl in MTBE (5v, freshly prepared by dissolving HCl gas in MTBE) to another flask and cooled it to 0±5° C., dropwise charged solution from step 8 (EtOH solution, 2 v) to the solution of MTBE (4 v)&2N HCl in MTBE (5 v) slowly below 5° C., stirred for 4 hours at 0-5° C., charged 5 v MTBE slowly, stir for 1 hour at 0-5° C., filtered, collected the cake and washed with 2 v MTBE, dried the cake under vacuum at 30±5° C. to afford compound 7-E as white solid (480 g, Yield ~80% for 3 steps; HPLC(ELSD)=98.5%).

Step 6b-2, charged compound 7-E and EtOH (7 v), cooled to 20±5° C., charged 50% NaOH aq. (10.0 eq. total NaOH is 5.0 eq), heated to 65-70° C., stirred at 60° C. for 12 hours, monitored by HPLC (ELSD) until compound 7-E≤0.5%, cooled to 0±5° C., adjusted pH=7-8 with 6N HCl at 0±5° C., stirred for 30 mins, filtered, collected the cake and washed it with 2 v EtOH, collected and combined the filtrate, used the filtrate as compound 8 to next step directly.

Step 6b-3, Charged the solution of compound 8 in EtOH to a flask, cooled to 10±5° C., charged NaBH$_4$ (4.0 eq.) at 10±5° C. in portions over 30 mins, stirred at 25±5° C. for 4 hours, monitored the reaction by HPLC-ELSD until the content of compound 8≤0.5%, cooled to 0±5° C., quenched the reaction with sat. NaHCO$_3$ (10 v), charged 20 v DCM, separation, extracted the aqueous with DCM/MeOH=5/1 (10 v), combined the organic layer, cooled it to 0±5° C., charged 2N HCl in MTBE (4.0 eq.), stirred at 20±5° C. for 3 hours, concentrated to 2 v, charged MTBE (10 v), concentrated to 4 v; the solution is cloudy, charged 6 v MTBE, cooled to 0±5° C.; stir at 0±5° C. for 1 hour, filtered, got crude product of compound 9-E (~500 g). Recrystallization procedure: dissolved crude compound 9-E in EtOH (2.5v) at 55±5° C. to afford clear solution, dropwise charged MTBE (7.5v) at 55±5° C., formed a cloudy solution, cooled to 10±5° C. over 2 hours, stirred at 10±5° C. for 2 hours, filtered and washed the cake with MTBE (40 mL, 1 v), dried the cake under vacuum at 30±5° C. to provide compound 9-E as white solid (270 g, 56% yield for two steps. HPLC (ELSD) purity 98.6%, HPLC purity by CAD 92.8%).

Example 7: Preparation of phenyl ((4-(tert-butyl)phenyl)sulfonyl)carbamate (10D)

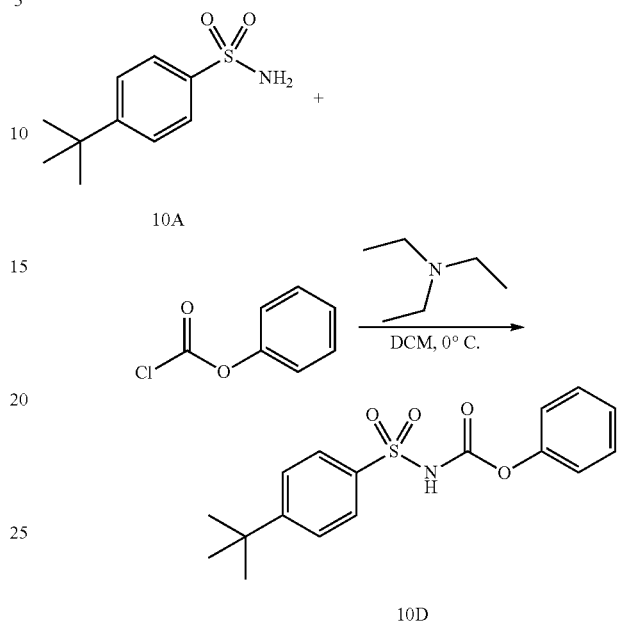

To a solution of 4-(tert-butyl)benzenesulfonamide 10A (20 g, 94 mmol) and triethylamine (32.7 ml, 234 mmol, 2.5 eq.) in dry DCM (200 mL) at 0° C. was added phenyl chloroformate (14.12 ml, 113 mmol, 1.2 eq.) portionwise. After stirring at 0° C. for 4-6 hrs, the reaction mixture was diluted with DCM (~300 mL) and washed with H$_2$O (2×200 mL), 10% citric acid (2×200 mL), brine (200 mL) and dried over Na$_2$SO$_4$. The organic layer was concentrated under reduced pressure at ~35° C. to ~100 mL. Lots of solid product crystallized out and the resulting slurry was allowed to cool to rt overnight. The solid precipitate was collected by filtration, rinsed with cold DCM (3×10 mL), dried to afford the desired product phenyl ((4-(tert-butyl)phenyl)sulfonyl) carbamate 10D (19.5 g, 75% yield). LC-MS, ES⁻ (m/z): 332.10 (M-1).

Example 8: Synthesis of Compound (III) from Compound 9-E

Method A:

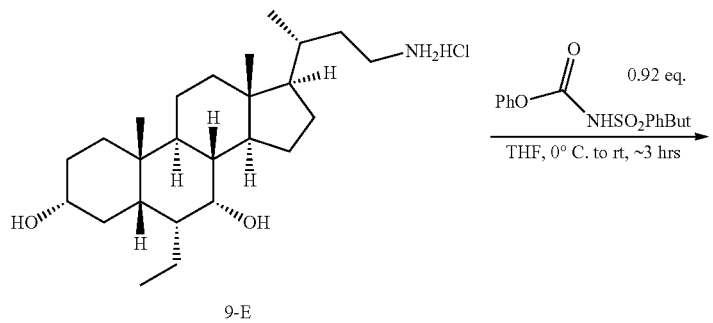

-continued

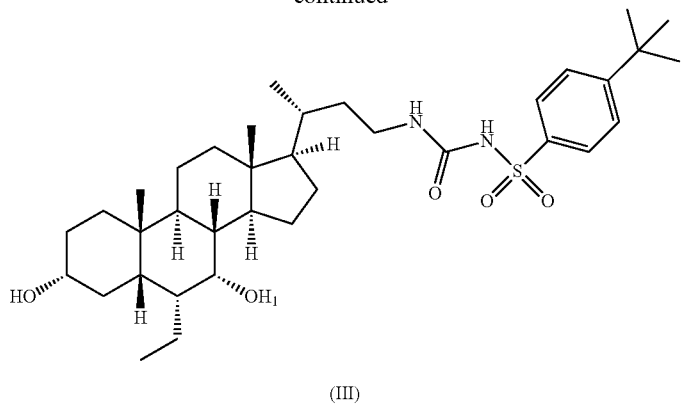

(III)

To a mixture of compound 9-E HCl salt (1 g, ~2.1 mmol) and triethylamine (0.83 mL, 5.99 mmol, 3 eq.) in dry THF (8 mL, 8v) at 0° C. was added phenyl ((4-(tert-butyl)phenyl)sulfonyl)carbamate (10D) (666 mg, 2.0 mmol, ~0.95 eq.). After stirring at 0° C. for ~5 min, the ice/water bath was removed and the reaction mixture was stirred at rt for ~3 hrs and monitored by HPLC and LC-MS. Upon completion, the reaction mixture was diluted with EtOAc (~30 mL). The organic layer was separated and washed with H₂O (30 mL), sat. NaHCO₃ (30 mL), H₂O (30 mL), 10% aqueous citric acid (2×30 mL), brine (30 mL), dried and concentrated to provide the crude compound (III) (1.4 g) which was used directly in the next step for the salt formation. LC-MS, ES⁻(m/z): 629.40 (M-1).
Method B:

To a 500 mL round bottom flask were charged compound 9-E (30 g, HCl salt, ~70 mmol, HPLC purity 92.8% by HPLC-CAD), toluene (6v, 180 mL) and isopropanol (3v, 90 mL) to form a white suspension, added triethylamine (30 mL, 3 eq.) to form a turbid mixture, cooled to ~5° C. with ice/water bath, charged compound 10D (22.2 g, 1 eq.) was added batch wise, slightly exothermic, temperature increased about 1° C., warm up to RT and stir at RT overnight. IPC by LC-MS and HPLC indicated reaction completion, dilute with ethylacetate (10v, 300 mL). Washed with 10% aq. citric acid (300 mL) and water (300 mL×2), the organic was dried with Na₂SO₄ and concentrated to afford crude compound (III) as white foam/gum (~65 g), which was used as is in next step.

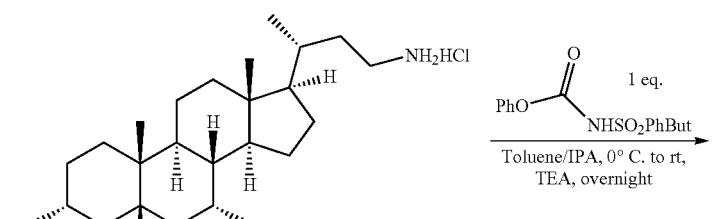

9-E

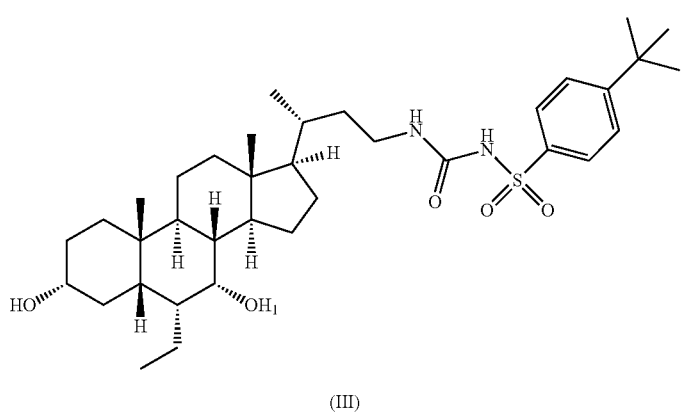

(III)

Example 9a: Synthesis of Compound 12, the Diethylamine Salt of Compound (III)

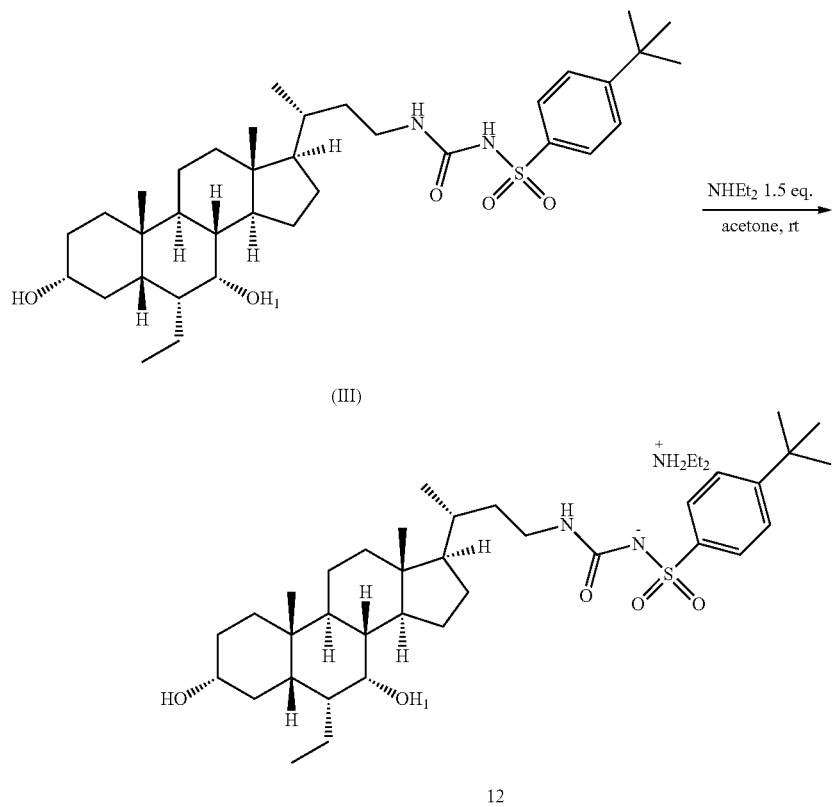

To a solution of compound (III) (1.4 g, ~2.1 mmol, crude product from the last step, Example 8, Method A) in acetone (7 mL, 5 v) was added diethylamine (0.31 mL, 3.0 mmol, 1.5 eq.). The resulting solution was sit at rt to allow crystal formation. After ~48 hrs, the resulting colorless crystalline solid was collected by filtration and rinsed with cold acetone (2×1.5 mL) to provide compound 12 as a colorless crystalline solid (1.1 g, ~67% yield from compound 8-E in 2 steps). LC-MS, ES$^-$(m/z): 629.40 (M-1).

Example 9b: Recrystallization of Compound 12

The compound 12 from Example 9a was dissolved in MeOH (~4v) to form a pale yellow solution, then the solution was concentrated under vacuum (bath ~35° C.), to afford a thick pale yellow syrup. Acetone (from ~8v to ~10V) was charged and the resulting mixture was heated to 35° C., and seeded with compound 12. The solution was then cooled to RT slowly and aged at RT for 18 h, filtered, washed with cold acetone. The wet cake was dried to afford compound 12 (HPLC purity 96.8% by HPLC-CAD) as a white solid. The product was characterized by X-ray powder diffraction (XRPD), thermogravimetric analysis (TGA) and differential scanning calorimetry (DSC).

Example 10: Synthesis of Compound (III) from Compound 12

Method A:

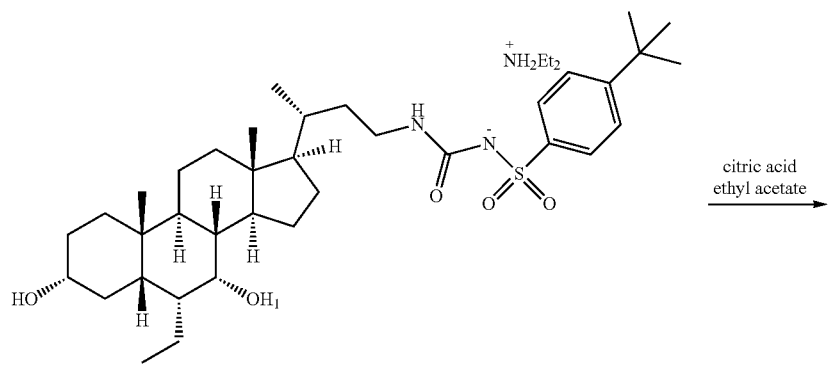
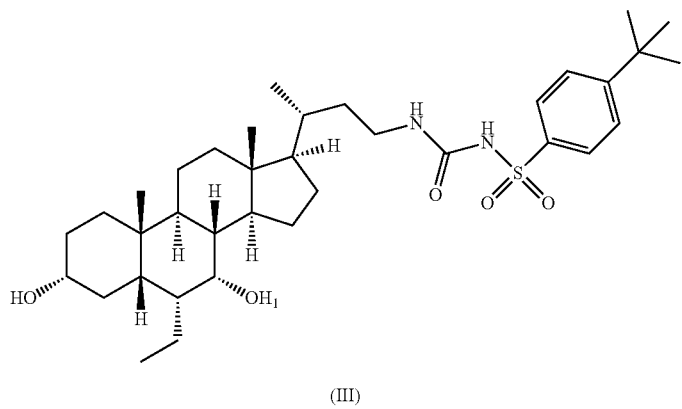
Compound 12 (500 mg, 0.71 mmol) was dissolved in EtOAc (20 mL, 40v) and washed with 10% citric acid (2×15 mL), H₂O (2×15 mL), brine (15 mL), dried over Na₂SO₄ and concentrated to dryness to afford compound (III) (440 mg, 98% yield) as a colorless solid. LC-MS, ES⁻ (m/z): 629.40 (M-1).
Method B:
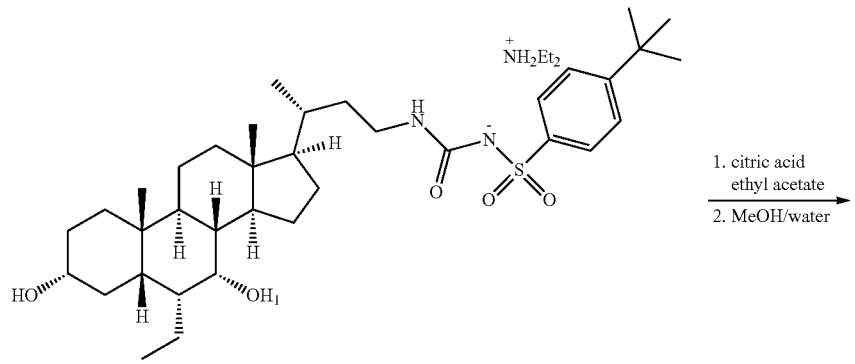

-continued

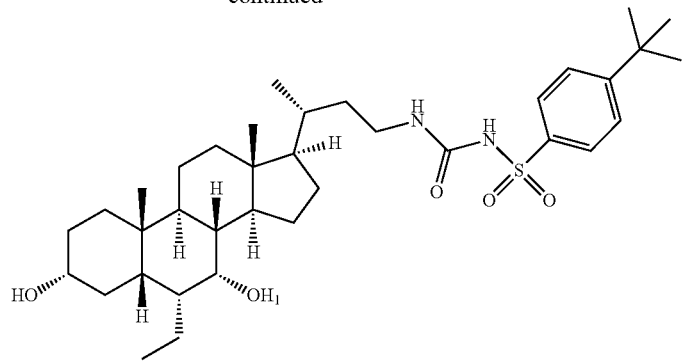

(III)

To reactor was charged with compound 12 (215 g), ethyl acetate (10v, 2.1 L) and 10% aqueous citric acid solution (6v, 1.2 L). The mixture was stirred for 15 mins and the layers were separated. The organic layer was washed with water (6 v X 2, 1.2 L X 2). The organic layer was then solvent exchanged to methanol (400 mL×3 times) under reduced pressure to afford methanol solution (~1 L). The solution was polish filtered through 0.2 m in-line filter. To jacketed reactor was charged water (3 L, ~15v) and heated to 40° C. The methanol solution was added slowly to form a white slurry. The white slurry was aged at 40° C. for 1 h, cooled to room temperature slowly and then further aged at room temperature for 18 h. This slurry was vacuum filtered through a frits funnel with filter paper and washed with water (~200 mL, ~1v) to afford a wet cake (407 g). The filter cake was dried at 37° C. under vacuum (with a small stream of $N_2$) for 48 h until constant weight to afford compound III (180.1 g, 94% yield) as a white solid. The XRPD pattern of the product indicates that it is an amorphous solid.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by one of Formulas 3-6,

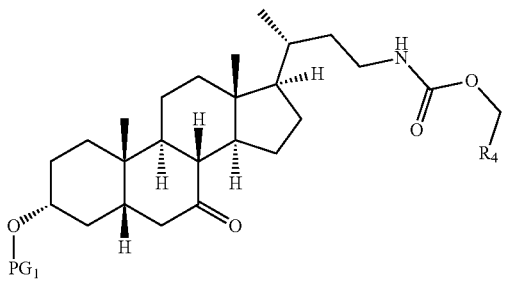

3

-continued

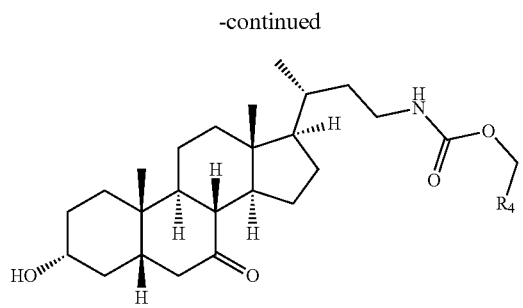

4

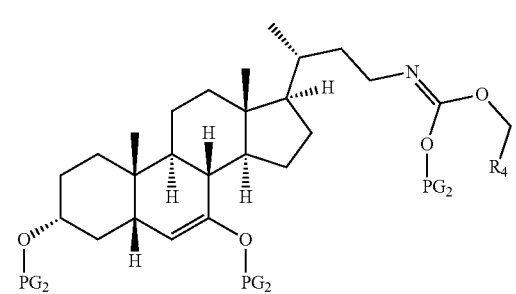

5

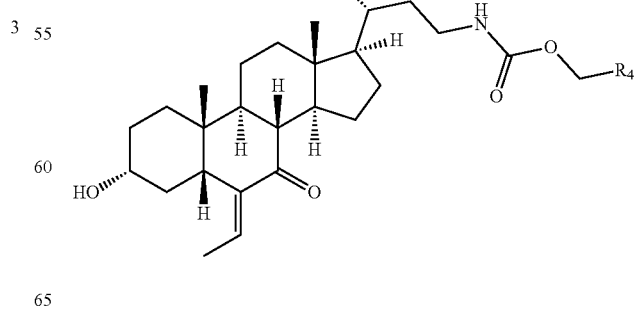

6 wherein $PG_1$ is a hydroxyl protecting group, $PG_2$ is a silyl group and $R_4$ is phenyl or substituted phenyl.

2. The compound of claim 1 represented by Formula 4,
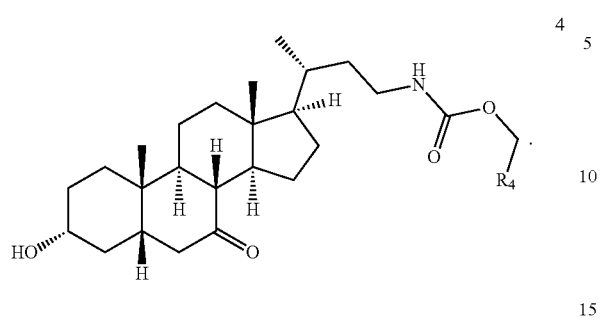
3. The compound of claim 1 represented by Formula 5,
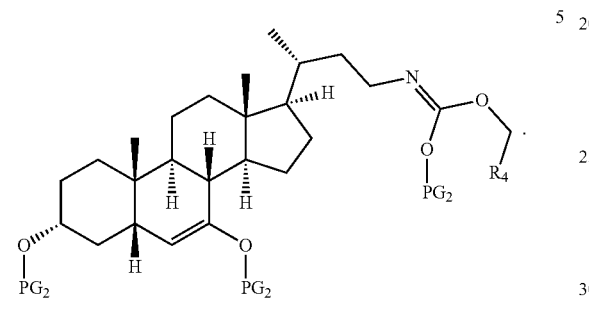
4. The compound of claim 1 represented by Formula 6,
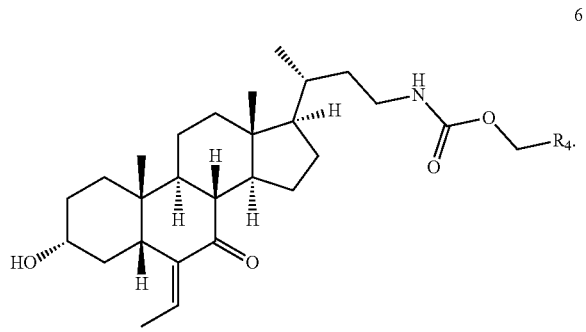
5. The compound of claim 1 represented by Formula 3,
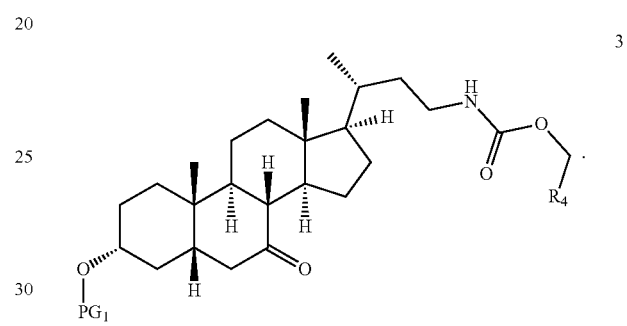
* * * * *